US011180756B2

(12) United States Patent
Oestergaard et al.

(10) Patent No.: US 11,180,756 B2
(45) Date of Patent: Nov. 23, 2021

(54) MORPHOLINO MODIFIED OLIGOMERIC COMPOUNDS

(71) Applicant: Ionis Pharmaceuticals, Inc., Carlsbad, CA (US)

(72) Inventors: Michael Oestergaard, Carlsbad, CA (US); Punit P. Seth, Carlsbad, CA (US)

(73) Assignee: Ionis Pharmaceuticals, Carlsbad, CA (US)

( * ) Notice: Subject to any disclaimer, the term of this patent is extended or adjusted under 35 U.S.C. 154(b) by 0 days.

(21) Appl. No.: 16/489,836

(22) PCT Filed: Mar. 9, 2018

(86) PCT No.: PCT/US2018/021768
§ 371 (c)(1),
(2) Date: Aug. 29, 2019

(87) PCT Pub. No.: WO2018/165564
PCT Pub. Date: Sep. 13, 2018

(65) Prior Publication Data
US 2020/0239881 A1    Jul. 30, 2020

Related U.S. Application Data

(60) Provisional application No. 62/481,439, filed on Apr. 4, 2017, provisional application No. 62/469,091, filed on Mar. 9, 2017.

(51) Int. Cl.
C12N 15/113    (2010.01)
C07F 9/6558    (2006.01)
C07F 9/6561    (2006.01)

(52) U.S. Cl.
CPC ........ *C12N 15/113* (2013.01); *C07F 9/65583* (2013.01); *C07F 9/65616* (2013.01); *C12N 2310/11* (2013.01); *C12N 2310/314* (2013.01); *C12N 2310/315* (2013.01); *C12N 2310/3233* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lableu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |

(Continued)

FOREIGN PATENT DOCUMENTS

| | | |
|---|---|---|
| EP | 0679657 | 11/1995 |
| WO | WO 1994/002499 | 2/1994 |

(Continued)

OTHER PUBLICATIONS

Zhang et al. Tetrahedron Letters 2008 vol. 49, pp. 3570-3573.*
Albaek et al., "Bi- and Tricyclic Nucleoside Derivatives Restricted in S-Type Conformations and Obtained by RCM-Reactions" Nucleosides, Nucleotides & Nucleic Acids (2003) 22(5-8):723-725.
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Altmann et al. "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides & Nucleotides (1997) 16: 917-926.

(Continued)

*Primary Examiner* — Tracy Vivlemore
(74) *Attorney, Agent, or Firm* — McNeill Baur PLC

(57) ABSTRACT

The present invention provides morpholino modified oligomeric compounds having at least one monomer subunit having Formula III, compounds having Formula I useful for making certain of the morpholino modified oligomeric compounds and methods of using the oligomeric compounds. In certain embodiments, the oligomeric compounds provided herein provide for an improved toxicity profile. Certain such oligomeric compounds are useful for hybridizing to a complementary nucleic acid, including but not limited, to nucleic acids in a cell. In certain embodiments, hybridization results in modulation of the amount of activity or expression of the target nucleic acid in a cell.

9 Claims, No Drawings
Specification includes a Sequence Listing.

(56) References Cited

U.S. PATENT DOCUMENTS

| | | |
|---|---|---|
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,426,220 B1 | 7/2002 | Bennett et al. |
| 6,600,032 B1 | 7/2003 | Manoharan et al. |
| 6,770,748 B2 | 8/2004 | Imanishi et al. |
| 6,794,499 B2 | 9/2004 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 2003/0082807 A1 | 5/2003 | Wengel |
| 2003/0207841 A1 | 11/2003 | Kaneko et al. |
| 2003/0224377 A1 | 12/2003 | Wengel et al. |
| 2004/0143114 A1 | 7/2004 | Imanishi et al. |
| 2004/0171570 A1 | 9/2004 | Allerson et al. |
| 2004/0192918 A1 | 9/2004 | Imanishi et al. |
| 2005/0130923 A1 | 6/2005 | Bhat et al. |
| 2011/0082289 A1 | 4/2011 | McGall et al. |
| 2012/0071641 A1 | 3/2012 | Manoharan et al. |
| 2014/0343123 A1* | 11/2014 | Prakash .............. C12N 15/113 514/44 A |
| 2016/0186175 A1 | 6/2016 | Seth et al. |
| 2019/0218236 A1 | 7/2019 | Caruthers et al. |

FOREIGN PATENT DOCUMENTS

| | | |
|---|---|---|
| WO | WO 1994/017093 | 8/1994 |
| WO | WO 1999/014226 | 3/1999 |
| WO | WO 2002/036743 | 5/2002 |
| WO | WO 2005/121371 | 12/2005 |
| WO | WO 2005/121372 | 12/2005 |
| WO | WO 2007/134181 | 11/2007 |
| WO | WO 2007/146511 | 12/2007 |
| WO | WO 2008/101157 | 8/2008 |
| WO | WO 2008/109080 | 9/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2011/133876 | 10/2011 |
| WO | 2018057430 A1 | 3/2018 |

OTHER PUBLICATIONS

Altmann et al. "Second Generation of Antisense Oligonucleotides: Structure-activity relationships and the design of improved signal-transduction inhibitors" RNA Interactions (1996) 24: 630-637.

Altmann et al. "Second Generation of Antisense Oligonucleotides: From Nuclease Resistance to Biological Efficacy in Animals" Chimia (1996) 168-176.

Altschul et al., "Basic Local Alignment Search Tool" J. Mol. Biol. (1990) 215 403-410.

Baker et al. "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J Biol Chem (1997) 272(18): 11994-12000.

Barany et al., "A New Amino Protecting Group Removable by Reduction. Chemistry of the Dithiasuccinoyl (Dts) Function" J. Am. Chem. Soc. (1977) 99:7363-7365.

Barany et al., "Kinetics and Mechanisms of the Thiolytic Removal of the Dithiasuccinoyl (Dts) Amino Protecting Group" J. Am. Chem. Soc. (1980) 102:3084-3095.

(56) References Cited

OTHER PUBLICATIONS

Bass, "Double-stranded RNA as a template for gene silencing" Cell (2000) 101:235-238.
Beaucage et al., "Advances in the Synthesis of Oligonucleotides by the Phosphoramidite Approach" Tetrahedron (1992) 48(12):2223-2311.
Beaucage et al., "The Functionalization of Oligonucleotides Via Phosphoramidite Derivatives" Tetrahedron (1993) 49(10):1925-1963.
Beaucage et al., "The Synthesis of Specific Ribonucleotides and Unrelated Phospholylated Biomolecules by the Phosphoramidite Method" Tetrahedron (1993) 49(46):10441-10488.
Belikova et al., "Synthesis of Ribonucleosides and Diribonucleoside Phosphates Containing 2-Chloro-Ethylamine and Nitrogen Mustard Residues" Tet. Lett. (1967) 37:3557-3562.
Braasch et al., "Locked nucleic acid (LNA): fine-tuning the recognition of DNA and RNA" Chem. Biol. (2001) 8:1-7.
Braasch et al., "Novel antisense and peptide nucleic acid strategies for controlling gene expression" Biochemistry (2002) 41: 4503-4510.
Brazma et al., "Gene expression data analysis" FEBS Letters (2000) 480:17-24.
Carulli et al., "High Throughput Analysis of Differential Gene Expression" J. Cell. Biochem. Suppl. (1998) 30:286-296.
Celis et al., "Gene expression profiling: monitoring transcription and translation products using DNA microarrays and proteomics" FEBS Lett (2000) 480:2-16.
Chiang et al., "Antisense Oligonucleotides Inhibit Intercellular Adhesion Molecule 1 Expression by Two Distinct Mechanisms" J. Biol. Chem. (1991) 266:18162-18171.
Conte et al. "Conformational properties and thermodynamics of the RNA duplex r(CGCAAAUUUGCG)2: comparison with the DNA analogue d(CGCAAATTTGCG)2" Nucleic Acids Research (1997) 25: 2627-2634.
Crooke et al., "Pharmacokinetic Properties of Several Novel Oligonucleotide Analogs in mice" J. Pharmacol. Exp. Ther. (1996) 277(2):923-937.
Egli et al., "Probing the Influence of Stereoelectronic Effects on the Biophysical Properties of Oligonucleotides: Comprehensive Analysis of the RNA Affinity, Nuclease Resistance, and Crystal Structure of Ten 2'-O-Ribonucleic Acid Modifications" Biochemistry (2005) 44(25):9045-9057.
Elayadi et al., "Application of PNA and LNA oligomers to chemotherapy" Curr. Opinion Invens. Drugs (2001) 2:558-561.
Elbashir, "Duplexes of 21-nucleotide RNAs mediate RNA interference in cultured mammalian cells" Nature (2001) 411:494-498.
Elbashir, "RNA interference is mediated by 21- and 22-nucleotide RNAs" Genes & Devel. (2001) 15:188-200.
Englisch et al., "Chemically Modified Oligonucleotides as Probes and Inhibitors" Agnew Chem. Int. Ed. Engl. (1991) 30:613-629.
Fire et al., "Potent and Specific Genetic Interference by Double-Stranded Rna in Caenorhabditis Elegans" Nature (1998) 391:806-811.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Fuchs et al., "Identification of Differentially Expressed Genes by Mutually Subtracted RNA Fingerprinting" Anal. Biochem. (2000) 286:91-98.
Gait et al., "Application of chemically synthesized RNA" RNA: Protein Interactions (1998) 1-36.
Gait, "Oligoribonucleotides" Antisense Research and Applications (1993), CRC Press, Boca Raton, pp. 289-301.
Gallo et al., "2'-C-Methyluridine Phosphoramidite: A New Building Block for the Preparation of RNA Analogues Carrying the 2'-Dydroxyl Group" Tetrahedron (2001) 57: 5707-5713.

Going et al., "Molecular Pathology and Future Developments" Eur. J. Cancer (1999) 35:1895-1904.
Jungblut et al., "Proteomics in human disease: Cancer, heart and infections diseases" Electrophoresis (1999) 20:2100-2110.
Jurecic et al., "Long-distance DD-PCR and cDNA microarrays" Curr. Opin. Microbiol. (2000) 3:316-321.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Kumar et al., "Design, synthesis, biophysical and primer extension studies of novel acyclic butyl nucleic acid (BuNA)" Org Biomol Chem (2013) 11: 5853-5865.
Larson et al., "Rapid DNA Fingerprinting of Pathogens by Flow Cytometry" Cytometry (2000) 41: 203-208.
Larsson et al., "High-throughput protein expression of cDNA products as a tool in functional genomics" J. Biotech. (2000) 80:143-157.
Lesnik et al. "Relative Thermodynamic Stability of DNA, RNA, and DNA:RNA Hybrid Duplexes: Relationship with Base Composition and Structure" Biochemistry (1995) 34: 10807-10815.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Madden et al., "Serial analysis of gene expression: from gene discovery to target identification" DDT (2000) 5:415-425.
Manoharan et al., "Chemical Modifications to Improve Uptake and Bioavailability of Antisense Oligonucleotides" Ann. N.Y. Acad. Sci. (1992) 660: 306-309.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Cholic Acid-Oligonucleotide Conjugates for Antisense Applications" Bioorg. Med. Chem. Lett. (1994) 4:1053-1060.
Manoharan et al., "Oligonucleotide Conjugates: Alteration of the Pharmacokinetic Properties of Antisense Agents" Nucleosides & Nucleotides (1995) 14(3-5):969-973.
Manoharan et al., "Lipidic Nucleic Acids" Tetrahedron Lett. (1995) 36(21):3651-3654.
Manoharan et al. "Oligonucleotide Conjugates as Potential Antisense Drugs with Improved Uptake, Biodistribution, Targeted Delivery, and Mechanism of Action" Antisense & Nucleic Acid Drug Development (2002) 12:103-128.
Martin et al. "A New Access to 2'O-Alkylated Ribonucleosides and Properties of 2'-O-Alkylated Oligoribonucleotides" Helvetica Chimica Acta (1995) 78: 486-504.
Mishra et al., "Improved leishmanicidal effect of phosphorotioate antisense oligonucleotides by LDL-mediated delivery" Biochim. Biophys. Acta (1995) 1264:229-237.
Miura et al., "Fluorometric determination of total mRNA with oligo(dT) immobilized on microtiter plates" Clin. Chem. (1996) 42:1758-1764.
Montgomery et al., "RNA as a target of double-stranded RNA-mediated genetic interference in Caenorhabditis elegans" Proc Natl. Acad. Sci. (1998) 95:15502-7.
Nishikura et al., "A Short Primer on RNAi: RNA-Directed RNA Polymerase Acts as a Key Catalyst" Cell (2001) 107:415-418.

(56) References Cited

OTHER PUBLICATIONS

Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: a promising molecular family for gene-function analysis and antisense drug development" Curr. Opinion Mol. Ther. (2001) 3:239-243.
Paul et al., "Synthesis of Phosphorodiamidate Morpholino Oligonucleotides and Their Chimeras Using Phosphoramidite Chemistry" J Am Chem Soc (2016) 138: 15663-15672.
Prashar et al., "READS: A Method for Display of 3'-End Fragment of Restriction Enzyme-Digested cDNAs for Analysis of Differential Gene Expression" Methods Enzymol. (1999) 303:258-272.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi, Chapter 15, Antisense Research and Applications, Crooke and Lebleu ed., CRC Press (1993).
Scaringe, "RNA Oligonucleotide Synthesis via 5'-Silyl-2'-Orthoester Chemistry" Methods (2001) 23:206-217.
Searle et al. "On the stability of nucleic acid structures in solution: enthalpy—entropy compensations, internal rotations and reversability" Nucleic Acids Research (1993) 21: 2051-2056.
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 455-456.
Singh et al., "Synthesis of 2'-amino-LNA: a novel conformationally restricted high-affinity oligonucleotide analogue with a handle" J. Org. Chem. (1998) 63: 10035-10039.
Singh et al. "Synthesis of Novel Bicyclo [2.2.1] Ribonucleosides: 2'-Amino- and 2'-Thio-LNA Monomeric Nucleosides" J Org Chem (1998) 63: 6078-6079.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Sutcliffe et al., "TOGA: An automated parsing technology for analyzing expression of nearly all genes" PNAS (2000) 97:1976-1981.
Svinarchuk et al., "Inhibition of HIV proliferation in MT-4 cells by antisense oligonucleotide conjugated to lipophilic groups" Biochimie (1993) 75:49-54.
Tabara et al., "RNAi in C. elegans: Soaking in the Genome Sequence" Science (1998) 282:430-431.
Tijsterman et al., "RNA hellcase MUT-14-dependent gene silencing triggered in C. elegans by short antisense RNAs" Science (2002) 295:694-7.
Timmons et al., "Ingestion of bacterially expressed dsRNAs can produce specific and potent genetic interference in Caenorhabditis Elegans" Gene (2001) 263:103-112.
Timmons et al., "Specific Interference by Ingested dsRNA" Nature (1998) 395:854.
To, "Identification of Differential Gene Expression by High Throughput Analysis" Comb. Chem. High Throughput Screen (2000) 3:235-241.
Tuschl et al., "Targeted mRNA degradation by double-stranded RNA in vitro" Genes Dev. (1999) 13:3191-7.
Wahlestedt et al., "Potent and nontoxic antisense oligonucleotide containing locked nucleic acids" Proc. Natl. Acad. Sci. USA (2000) 97: 5633-5638.
Wouters et al., "5-Substituted Pyrimidine 1,5-Anhydrohexitols: Conformational Analysis and Interaction with Viral Thymidine Kinase" Bioorg. Med. Chem. Lett. (1999) 9:1563-1566.
Zamecnik et al., "Inhibition of Rous sarcoma virus replication and cell transformation by a specific oligodeoxynucleotide" PNAS (1978) 75:280-284.
Zhang et al., "RNA interference in mammalian cells by siRNAs modified with morpholino nucleoside analogues" Bioorganic & Medicinal Chemistry (2009) 17: 2441-2446.
Zhang et al., "PowerBLAST: A New Network BLAST Application for Interactive or Automated Sequence Analysis and Annotation" Genome Res. (1997) 7:649-656.
Zhang et al., "Synthesis and properties of morpholino chimeric oligonucleotides" Tetrahedron Letters (2008) 49: 3570-3573.
Zhou et al., "Double sugar and phosphate backbone-constrained nucleotides: synthesis, structure, stability and their incorporation into oligodeoxynucleotides" J. Org. Chem. (2009) 74(1):3248-3265.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
International Search Report for PCT/US18/021768 dated Jun. 20, 2018.
Langner et al., "Synthesis and Characterization of Thiophosphoramidate Morpholino Oligonucleotides and Chimeras" J Am Chem Soc (2020) 142: 16240-16253.

* cited by examiner

SEQUENCE LISTING

<160> NUMBER OF SEQ ID NOS: 8

<210> SEQ ID NO 1
<211> LENGTH: 3160
<212> TYPE: DNA
<213> ORGANISM: Homo Sapiens

<400> SEQUENCE: 1

```
cctccctcg cccggcgcgg tcccgtccgc ctctcgctcg cctcccgcct ccctcggtc      60 ttccgaggcg cccgggctcc cggcgcggcg gcggaggggg cgggcaggcc ggcgggcggt    120
gatgtggcag gactctttat gcgctgcggc aggatacgcg ctcggcgctg ggacgcgact    180
gcgctcagtt ctctcctctc ggaagctgca gccatgatgg aagtttgaga gttgagccgc    240
tgtgaggcga ggccgggctc aggcgaggga gatgagagac ggcggcggcc gcggcccgga    300
gcccctctca gcgcctgtga gcagccgcgg gggcagcgcc ctcggggagc cggccggcct    360 gcggcggcg cagcggcggc gtttctgcc tcctcttcgt cttttctaac cgtgcagcct      420
cttcctcggc ttctcctgaa agggaaggtg gaagccgtgg gctcgggcgg gagccggctg    480
aggcgcggcg gcggcggcgg cggcacctcc cgctcctgga gcggggggga gaagcggcgg    540
cggcggcggc cgcggcggct gcagctccag ggaggggtc tgagtcgcct gtcaccattt     600
ccagggctgg gaacgccgga gagttggtct ctcccttct actgcctcca acacggcggc    660
ggcggcggcg gcacatccag ggacccgggc cggttttaaa cctcccgtcc gccgccgccg    720 cacccccgt ggcccgggct ccggaggccg ccggcggagg cagccgttcg gaggattatt     780
cgtcttctcc ccattccgct gccgccgctg ccaggcctct ggctgctgag gagaagcagg    840
cccagtcgct gcaaccatcc agcagccgcc gcagcagcca ttacccggct gcggtccaga    900
gccaagcggc ggcagagcga ggggcatcag ctaccgccaa gtccagagcc atttccatcc    960
tgcagaagaa gccccgccac cagcagcttc tgccatctct ctcctccttt ttcttcagcc   1020
acaggctccc agacatgaca gccatcatca aagagatcgt tagcagaaac aaaaggagat   1080
atcaagagga tggattcgac ttagacttga cctatattta tccaaacatt attgctatgg   1140
```

```
gatttcctgc agaaagactt gaaggcgtat acaggaacaa tattgatgat gtagtaaggt    1200
ttttggattc aaagcataaa aaccattaca agatatacaa tctttgtgct gaaagacatt    1260
atgacaccgc caaatttaat tgcagagttg cacaatatcc ttttgaagac cataacccac    1320
cacagctaga acttatcaaa ccctttttgtg aagatcttga ccaatggcta agtgaagatg    1380
acaatcatgt tgcagcaatt cactgtaaag ctggaaaggg acgaactggt gtaatgatat    1440
gtgcatattt attacatcgg ggcaaatttt taaaggcaca agaggcccta gatttctatg    1500
gggaagtaag gaccagagac aaaaagggag taactattcc cagtcagagg cgctatgtgt    1560
attattatag ctacctgtta aagaatcatc tggattatag accagtggca ctgttgtttc    1620
acaagatgat gtttgaaact attccaatgt tcagtggcgg aacttgcaat cctcagtttg    1680
tggtctgcca gctaaaggtg aagatatatt cctccaattc aggacccaca cgacgggaag    1740
acaagttcat gtactttgag ttccctcagc cgttacctgt gtgtggtgat atcaaagtag    1800
agttcttcca caaacagaac aagatgctaa aaaaggacaa aatgtttcac ttttgggtaa    1860
atacattctt cataccagga ccagaggaaa cctcagaaaa agtagaaaat ggaagtctat    1920
gtgatcaaga aatcgatagc atttgcagta tagagcgtgc agataatgac aaggaatatc    1980
tagtacttac tttaacaaaa aatgatcttg acaaagcaaa taaagacaaa gccaaccgat    2040
acttttctcc aaatttttaag gtgaagctgt acttcacaaa aacagtagag gagccgtcaa    2100
atccagaggc tagcagttca acttctgtaa caccagatgt tagtgacaat gaacctgatc    2160
attatagata ttctgacacc actgactctg atccagagaa tgaacctttt gatgaagatc    2220
agcatacaca aattacaaaa gtctgaattt ttttttatca agagggataa acaccatga    2280 aaataaactt gaataaactg aaaatggacc ttttttttttt taatggcaat aggacattgt    2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460 tatataccctt tttgtgtcaa aaggacattt aaaattcaat taggattaat aaagatggca    2520
ctttcccgtt ttattccagt tttataaaaa gtggagacag actgatgtgt atacgtagga    2580
attttttcct tttgtgttct gtcaccaact gaagtggcta aagagctttg tgatatactg    2640
gttcacatcc tacccctttg cacttgtggc aacagataag tttgcagttg gctaagagag    2700
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga acacagcaa caatgactta    3060 accatataaa tgtggaggct atcaacaaag aatgggcttg aaacattata aaaattgaca    3120
atgatttatt aaatatgttt tctcaattgt aaaaaaaaaa                          3160
```

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2

```
aatggctaag tgaagatgac aatcat                                              26

<210> SEQ ID NO 3
<211> LENGTH: 25
<212> TYPE: DNA
<213> ORGANISM: Artificial sequence
<220> FEATURE:
<223> OTHER INFORMATION: Primer

<400> SEQUENCE: 3
tgcacatatc attacaccag ttcgt                                               25

<210> SEQ ID NO 4
<211> LENGTH: 30
<212> TYPE: DNA
<213> ORGANISM: Artificial sequence
<220> FEATURE:
<223> OTHER INFORMATION: Probe

<400> SEQUENCE: 4
ttgcagcaat tcactgtaaa gctggaaagg                                          30

<210> SEQ ID NO 5
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 5
uaaugugaga acaugc                                                         16

<210> SEQ ID NO 6
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 6
gcatgttctc acatta                                                         16

<210> SEQ ID NO 7
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 7
agcaaaaaac gc                                                             12

<210> SEQ ID NO 8
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 8 gcgtttttg ct                                                              12
```

MORPHOLINO MODIFIED OLIGOMERIC COMPOUNDS

FIELD OF THE INVENTION

The present invention pertains generally to chemically-modified oligonucleotides for use in research, diagnostics, and/or therapeutics.

SEQUENCE LISTING

The present application is being filed along with a Sequence Listing in electronic format. The Sequence Listing is provided as a file entitled CHEM0098USASEQ_ST25.txt, created Aug. 29, 2019, which is 6 Kb in size. The information in the electronic format of the sequence listing is incorporated herein by reference in its entirety.

BACKGROUND OF THE INVENTION

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances, antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. An additional example of modulation of RNA target function by an occupancy-based mechanism is modulation of microRNA function. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense technology is an effective means for reducing the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, pharmacokinetics or affinity for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

Targeting disease-causing gene sequences was first suggested more than thirty years ago (Belikova et al., *Tet. Lett.* 1967, 8(37), 3557-3562), and antisense activity was demonstrated in cell culture more than a decade later (Zamecnik et al., *Proc. Natl. Acad. Sci. U.S.A.* 1978, 75(1), 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Morpholino compounds and their use in oligomeric compounds has been reported in numerous patents and published articles (see for example: Braasch et al., *Biochemistry*, 2002, 41, 4503-4510; and U.S. Pat. Nos. 5,698,685; 5,166,315; 5,185,444; and 5,034,506).

The synthesis and properties of morpholino chimeric oligonucleotides has been previously reported (Zhang et al., Tetrahedron Letters, 2008, 49, 3570-3573).

The interference in mammalian cells by siRNA's modified with morpholino nucleoside analogues has been previously reported (Zang et al., Bioorganic & Medicinal Chemistry, 2009, 17, 2441-2446).

The synthesis of phosphorodiamidate morpholino oligonucleotides and their chimeras using phosphoramidite chemistry has been previously reported (Paul et al., J. A. C. S., 2016, 138(48), 15663-15672).

SUMMARY OF THE INVENTION

In certain embodiments, oligomeric compounds are provided having at least one monomer subunit having Formula III, compounds having Formula I useful for making the oligomeric compounds and methods of using the oligomeric compounds.

In certain embodiments, compounds are provided having Formula I:

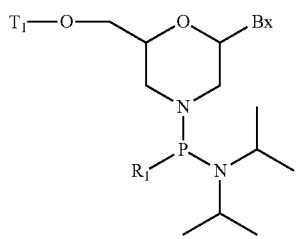

wherein:
Bx is an optionally protected heterocyclic base moiety;
$T_1$ is H or a hydroxyl protecting group; and
$R_1$ is $C_{1-6}$ alkyl or substituted $C_{1-6}$ alkyl comprising an optionally protected substituent group selected from halogen, $OJ_1$, $NJ_1J_2$, $SJ_1$, $N_3$, $OC(=Q)J_1$, $OC(=Q)NJ_1J_2$, $NJ_3C(=Q)NJ_1J_2$ and CN, wherein each $J_1$, $J_2$ and $J_3$ is, independently, H or $C_1$-$C_6$ alkyl, and Q is O, S or $NJ_1$.

In certain embodiments, Bx is uracil, thymine, cytosine, 4-N-benzoylcytosine, 4-N-isobutyrylcytosine, 5'-methyl cytosine, 5'-methyl-4-N-benzoylcytosine, 5'-methyl-4-N-isbutyrylcytosine, adenine, 6-N-benzoyladenine, guanine or 2-N-isobutyrylguanine. In certain embodiments, Bx is uracil, thymine, 5'-methyl-4-N-isbutyrylcytosine, 6-N-benzoyladenine or 2-N-isobutyrylguanine.

In certain embodiments, $T_1$ is 4,4'-dimethoxytrityl.

In certain embodiments, $R_1$ is $C_{1-6}$ alkyl. In certain embodiments, $R_1$ is methyl. In certain embodiments, $R_1$ is a substituted $C_{1-6}$ alkyl. In certain embodiments, the substituted $C_{1-6}$ alkyl is substituted with $OJ_1$ wherein $J_1$ is $C_1$-$C_6$ alkyl. In certain embodiments, $R_1$ is —$(CH_2)_3$—$OCH_3$.

In certain embodiments, oligomeric compounds are provided comprising from 10 to 30 monomer subunits wherein at least one monomer subunit has Formula III:

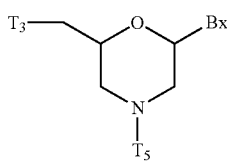

wherein independently for each monomer subunit having Formula III:
Bx is an optionally protected heterocyclic base moiety;
$T_3$ is hydroxyl, a protected hydroxyl, an internucleoside linking group linking the monomer subunit of Formula III to the 5'-remainder of the oligomeric compound or a terminal group;
$T_5$ is H, $C_{1-6}$ alkyl, a terminal group or a nitrogen protecting group when located on the 3'-terminus of the oligomeric compound wherein at least one $T_5$ is a linking group having the formula:

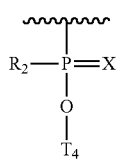

wherein independently for each $T_5$:
$R_2$ is hydroxyl, $C_{1-6}$ alkyl or substituted $C_{1-6}$ alkyl comprising an optionally protected substituent group selected from halogen, $OJ_1$, $NJ_1J_2$, $SJ_1$, $N_3$, $OC(=Q)J_1$, $OC(=Q)NJ_1J_2$, $NJ_3C(=Q)NJ_1J_2$ and CN, wherein each $J_1$, $J_2$ and $J_3$ is, independently, H or $C_1$-$C_6$ alkyl, and Q is O, S or $NJ_1$;
X is O or S wherein when X is O, at least one $R_2$ is other than hydroxyl; and
$T_4$ is a single bond connecting said linking group to the 3'-remainder of the oligomeric compound or $T_4$ forms a single bond with a $T_3$ from a second monomer subunit having Formula III.

In certain embodiments, each Bx is, independently, an optionally protected pyrimidine, substituted pyrimidine, purine or substituted purine. In certain embodiments, each Bx is, independently, uracil, thymine, cytosine, 4-N-benzoylcytosine, 4-N-isobutyrylcytosine, 5'-methyl cytosine, 5'-methyl-4-N-benzoylcytosine, 5'-methyl-4-N-isbutyrylcytosine, adenine, 6-N-benzoyladenine, guanine or 2-N-isobutyrylguanine. In certain embodiments, each Bx is, independently, uracil, thymine, cytosine, 5-methylcytosine, adenine or guanine.

In certain embodiments, at least one $T_3$ is an internucleoside linking group linking the monomer subunit of Formula III to the 5'-remainder of the oligomeric compound. In certain embodiments, one $T_3$ is hydroxyl. In certain embodiments, one $T_3$ is a terminal group.

In certain embodiments, one $T_5$ is H, $C_1$-$C_6$ alkyl or a nitrogen protecting group. In certain embodiments, one $T_5$ is a methyl. In certain embodiments, one $T_5$ is 4,4'-dimethoxytrityl. In certain embodiments, one $T_5$ is a terminal group. In certain embodiments, one $T_5$ is said linking group. In certain embodiments, each $T_5$ is said linking group.

In certain embodiments, at least one $T_4$ is a single bond connecting said linking group to the 3'-remainder of the oligomeric compound. In certain embodiments, at least one $T_4$ forms a single bond with a $T_3$ from a second monomer subunit having Formula III.

In certain embodiments, the 5'-remainder of the oligomeric compound comprises a 3'-terminal 3-D-2'-deoxyribonucleoside. In certain embodiments, the 3'-remainder of the oligomeric compound comprises a 5'-terminal 3-D-2'-deoxyribonucleoside. In certain embodiments, at least one of the 5'-terminal monomer and the 3'-terminal monomer of the oligomeric compound comprises a terminal group.

In certain embodiments, each X is O. In certain embodiments, each X is S.

In certain embodiments, each $R_2$ is hydroxyl. In certain embodiments, each $R_2$ is $C_{1-6}$ alkyl. In certain embodiments, each $R_2$ is methyl. In certain embodiments, each $R_2$ is substituted $C_{1-6}$ alkyl. In certain embodiments, the substituent group is $OJ_1$. In certain embodiments, $J_1$ is $C_1$-$C_6$ alkyl. In certain embodiments, $J_1$ is methyl. In certain embodiments, each $R_2$ is —$(CH_2)_3$—$OCH_3$.

In certain embodiments, essentially each monomer subunit has Formula III.

In certain embodiments, oligomeric compounds are provided comprising a gapped oligomeric compound having a first region consisting of from 2 to 5 monomer subunits, a second region consisting of from 2 to 5 monomer subunits and a gap region located between the first and second region consisting of from 8 to 12 monomer subunits wherein each monomer subunit in the first and second region is a modified nucleoside and each monomer subunit in the gap region is an unmodified nucleoside or a modified nucleoside different from the modified nucleosides in the first and second region and wherein at least one of the monomer subunits has Formula III. In certain embodiments, each monomer subunit in the gap region other than monomer subunits having Formula III is a β-D-2'-deoxyribonucleoside. In certain embodiments, each monomer subunit in the gap region is a β-D-2'-deoxyribonucleoside.

In certain embodiments, one monomer subunit having Formula III in the gap region. In certain embodiments, two monomer subunits having Formula III in the gap region. In certain embodiments, three monomer subunits having Formula III in the gap region.

In certain embodiments, at least one monomer subunit having Formula III in one of the first and second regions. In certain embodiments, at two monomer subunits having Formula III in the first and second regions. In certain embodiments, 3 to 4 monomer subunits having Formula III in the first and second regions.

In certain embodiments, the gap region has from about 10 to about 12 monomer subunits. In certain embodiments, the gap region has 10 monomer subunits.

In certain embodiments, the first and second regions each comprise 2 monomer subunits. In certain embodiments, the first and second regions each comprise 3 monomer subunits. In certain embodiments, the first and second regions each comprise 5 monomer subunits. In certain embodiments, each modified nucleoside in the first and second region comprises a modified sugar moiety. In certain embodiments, each modified nucleoside in the first and second region comprises the same modified sugar moiety.

In certain embodiments, at least two modified nucleosides in the first and second region comprises differently modified sugar moieties. In certain embodiments, each modified nucleoside in the first and second region is, independently, a bicyclic nucleoside comprising a bicyclic furanosyl sugar moiety or a modified nucleoside comprising a furanosyl sugar moiety having at least one substituent group. In certain embodiments, each modified nucleoside in the first and second region is, independently, a bicyclic nucleoside comprising a 4'-CH((S)—CH$_3$)—O-2' bridge or a 2'-O-methoxyethyl substituted nucleoside. In certain embodiments, at least one modified nucleoside in the first and second region comprises a sugar surrogate.

In certain embodiments, each internucleoside linking group other than a linking group ($T_5$) is, independently, a phosphodiester internucleoside linking group or a phosphorothioate internucleoside linking group. In certain embodiments, essentially each internucleoside linking group other than a linking group ($T_5$) is a phosphorothioate internucleoside linking group.

In certain embodiments, oligomeric compounds are provided comprising from 12 to 28 monomer subunits comprising at least one $T(Z_aT_b)_cZ_d$ motif where each a and b is, independently, from 1 to about 8, c is from 1 to about 12, d is 0 or 1, one of T and Z is a β-D-2'-deoxyribonucleoside and the other of T and Z is a monomer subunit having Formula III:

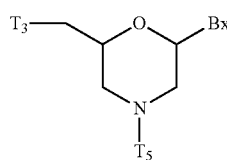

wherein independently for each monomer subunit having Formula III:
Bx is an optionally protected heterocyclic base moiety;
$T_3$ is hydroxyl, a protected hydroxyl, an internucleoside linking group linking the monomer subunit of Formula III to the 5'-remainder of the oligomeric compound or a terminal group;
$T_5$ is H, $C_{1-6}$ alkyl, a nitrogen protecting or a linking group having the formula:

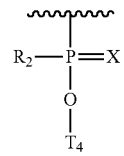

wherein independently for each $T_5$:
$R_2$ is hydroxyl, $C_{1-6}$ alkyl or substituted $C_{1-6}$ alkyl comprising an optionally protected substituent group selected from halogen, $OJ_1$, $NJ_1J_2$, $SJ_1$, $N_3$, $OC(=Q)J_1$, $OC(=Q)NJ_1J_2$, $NJ_3C(=Q)NJ_1J_2$ and CN, wherein each $J_1$, $J_2$ and $J_3$ is, independently, H or $C_1$-$C_6$ alkyl, and Q is O, S or $NJ_1$;
X is O or S; and
$T_4$ is a single bond connecting said linking group to the 3'-remainder of the oligomeric compound or $T_4$ forms a single bond with a $T_3$ from a second monomer subunit having Formula III.

In certain embodiments, each Bx is, independently, an optionally protected pyrimidine, substituted pyrimidine, purine or substituted purine. In certain embodiments, each Bx is, independently, uracil, thymine, cytosine, 5-methylcytosine, adenine or guanine.

In certain embodiments, each X is O. In certain embodiments, each X is S.

In certain embodiments, each $R_2$ is hydroxyl. In certain embodiments, each $R_2$ is $C_{1-6}$ alkyl. In certain embodiments, each $R_2$ is methyl. In certain embodiments, each $R_2$ is substituted $C_{1-6}$ alkyl.

In certain embodiments, the substituent group is $OJ_1$. In certain embodiments, $J_1$ is $C_1$-$C_6$ alkyl. In certain embodiments, $J_1$ is methyl. In certain embodiments, each $R_2$ is —(CH$_2$)$_3$—OCH$_3$.

In certain embodiments, oligomeric compounds are provided comprising one $T(Z_aT_b)_cZ_d$ motif. In certain embodiments, oligomeric compounds are provided comprising two $T(Z_aT_b)_cZ_d$ motifs separated by a central region of from 2 to 14 nucleosides. In certain embodiments, oligomeric compounds are provided comprising at least three $T(Z_aT_b)_cZ_d$ motifs wherein each $T(Z_aT_b)_cZ_d$ motif is separated by at least 1 nucleoside.

In certain embodiments, each a and b is 1. In certain embodiments, each a and b is, independently, from 1 to 3. In certain embodiments, each a and b is, independently, from 1 to 5. In certain embodiments, each a and b is, independently, from 1 to 7.

In certain embodiments, c is 1. In certain embodiments, c is 2. In certain embodiments, c is 3. In certain embodiments, c is from 4 to 6.

In certain embodiments, d is 0. In certain embodiments, d is 1.

In certain embodiments, T is a β-D-2'-deoxyribonucleoside.

In certain embodiments, Z is a β-D-2'-deoxyribonucleoside.

In certain embodiments, each internucleoside linking group other than a linking group ($T_5$) is, independently, a phosphodiester internucleoside linking group or a phosphorothioate internucleoside linking group. In certain embodiments, each internucleoside linking group other than a linking group ($T_5$) is a phosphorothioate internucleoside linking group.

In certain embodiments, the oligomeric compound comprises at least from 1 to 3 3'-terminal β-D-2'-deoxyribonucleoside. In certain embodiments, the oligomeric compound comprises at least from 1 to 3 5'-terminal β-D-2'-deoxyribonucleosides. In certain embodiments, the oligomeric compound comprises a 5' or 3'-terminal group.

In certain embodiments, the oligomeric compound comprises from 12 to 22 monomer subunits. In certain embodiments, the oligomeric compound comprises from 14 to 20 monomer subunits. In certain embodiments, the oligomeric compound comprises from 14 to 16 monomer subunits. In certain embodiments, the oligomeric compound comprises from 16 to 20 monomer subunits.

In certain embodiments, oligomeric compounds are provided comprising from 10 to 30 monomer subunits wherein at least one monomer subunit has Formula II:

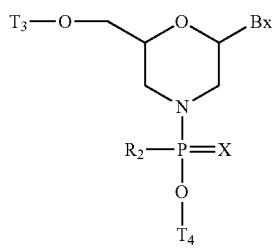

wherein independently for each monomer subunit having Formula II:

Bx is an optionally protected heterocyclic base moiety;

$T_3$ is H, a hydroxyl protecting group, an internucleoside linking group linking the monomer subunit of Formula II to the 5'-remainder of the oligomeric compound or a terminal group;

$T_4$ is a single bond connecting the monomer subunit having Formula II to the 3'-remainder of the oligomeric compound;

$R_2$ is HO, $C_{1-6}$ alkyl or substituted $C_{1-6}$ alkyl comprising an optionally protected substituent group selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$; and X is O or S wherein when X is O, $R_2$ is other than OH.

In certain embodiments, oligomeric compounds are provided comprising from 10 to 30 monomer subunits wherein at least one monomer subunit has Formula II:

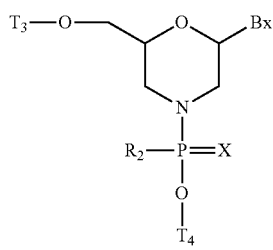

wherein independently for each monomer subunit having Formula II:

Bx is an optionally protected heterocyclic base moiety;

$T_3$ is H, a hydroxyl protecting group, an internucleoside linking group linking the monomer subunit of Formula II to the 5'-remainder of the oligomeric compound or a terminal group;

$T_4$ is a single bond connecting the monomer subunit having Formula II to the 3'-remainder of the oligomeric compound;

$R_2$ is HO, $C_{1-6}$ alkyl or substituted $C_{1-6}$ alkyl comprising an optionally protected substituent group selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$; and X is O or S wherein when X is O and $R_2$ is OH then the oligomeric compound is other than an siRNA oligomeric compound.

In certain embodiments, each Bx is, independently, an optionally protected pyrimidine, substituted pyrimidine, purine or substituted purine. In certain embodiments, Bx is, independently, uracil, thymine, cytosine, 5-methylcytosine, adenine or guanine.

In certain embodiments, at least one $T_3$ is an internucleoside linking group linking the monomer subunit of Formula II to the 5'-remainder of the oligomeric compound.

In certain embodiments, the 5'-remainder of the oligomeric compound comprises a 3'-terminal β-D-2'-deoxyribonucleoside.

In certain embodiments, one $T_3$ is H. In certain embodiments, one $T_3$ is a terminal group.

In certain embodiments, the 3'-remainder of the oligomeric compound comprises a 5'-terminal β-D-2'-deoxyribonucleoside. In certain embodiments, the 5'-terminal monomer of the 5'-remainder of the oligomeric compound or the 3'-terminal monomer of the 3'-remainder of the oligomeric compound comprises a terminal group.

In certain embodiments, each X is O. In certain embodiments, each X is S.

In certain embodiments, each $R_2$ is OH. In certain embodiments, each $R_2$ is $C_{1-6}$ alkyl. In certain embodiments, each $R_2$ is methyl. In certain embodiments, each $R_2$ is substituted $C_{1-6}$ alkyl. In certain embodiments, the substituent group is $OJ_1$. In certain embodiments, $J_1$ is $C_1$-$C_6$ alkyl. In certain embodiments, $J_1$ is methyl. In certain embodiments, each $R_2$ is —$(CH_2)_3$—$OCH_3$.

In certain embodiments, essentially each monomer subunit has Formula II.

In certain embodiments, the oligomeric compound comprises a gapped oligomeric compound having a first region consisting of from 2 to 5 monomer subunits, a second region consisting of from 2 to 5 monomer subunits and a gap region located between the first and second region consisting of from 8 to 12 monomer subunits wherein each monomer subunit in the first and second region is a modified nucleoside and each monomer subunit in the gap region is an unmodified nucleoside or a modified nucleoside different from the modified nucleosides in the first and second region and wherein at least one of the monomer subunits has Formula II.

In certain embodiments, gapped oligomeric compounds are provided wherein monomer subunits of Formula II are located at one or more positions that don't include a gap junction.

In certain embodiments, each monomer subunit in the gap region other than a monomer subunit having Formula II is a β-D-2'-deoxyribonucleoside. In certain embodiments, each monomer subunit in the gap region is a β-D-2'-deoxyribonucleoside.

In certain embodiments, the oligomeric compound comprises one monomer having Formula II in the gap region. In certain embodiments, the oligomeric compound comprises two monomers having Formula II in the gap region. In certain embodiments, the oligomeric compound comprises three monomers having Formula II in the gap region.

In certain embodiments, the oligomeric compound comprises at least one monomer having Formula II in one of the first and second regions. In certain embodiments, the oligomeric compound comprises at least two monomers having Formula II in the first and second regions. In certain embodiments, the oligomeric compound comprises from 3 to 4 monomers having Formula II in the first and second regions.

In certain embodiments, the gap region has from about 10 to about 12 monomer subunits. In certain embodiments, the gap region has 10 monomer subunits.

In certain embodiments, the first and second regions each comprise 2 monomer subunits. In certain embodiments, the first and second regions each comprise 3 monomer subunits. In certain embodiments, the first and second regions each comprise 5 monomer subunits. In certain embodiments, each modified nucleoside in the first and second region comprises a modified sugar moiety. In certain embodiments, each modified nucleoside in the first and second region comprises the same type of modified sugar moiety. In certain embodiments, at least two modified nucleosides in the first and second region comprises differently modified sugar moieties. In certain embodiments, each modified nucleoside in the first and second region is, independently, a bicyclic nucleoside comprising a bicyclic furanosyl sugar moiety or a modified nucleoside comprising a furanosyl sugar moiety having at least one substituent group. In certain embodiments, each modified nucleoside in the first and second region is, independently, a bicyclic nucleoside comprising a 4'-CH((S)—CH$_3$)—O-2' bridge or a 2'-O-methoxyethyl substituted nucleoside. In certain embodiments, at least one modified nucleoside in the first and second region comprises a sugar surrogate.

In certain embodiments, each internucleoside linking group other than a linking group included in a monomer subunit having Formula II is, independently, a phosphodiester internucleoside linking group or a phosphorothioate internucleoside linking group. In certain embodiments, essentially each internucleoside linking group other than a linking group included in a monomer subunit having Formula II is a phosphorothioate internucleoside linking group.

In certain embodiments, methods of inhibiting gene expression are provided comprising contacting one or more cells, a tissue or an animal with an oligomeric compound as disclosed herein that is complementary to a target RNA.

In certain embodiments, the cells are in a human. In certain embodiments, the target RNA is human mRNA. In certain embodiments, the target RNA is cleaved thereby inhibiting its function.

In certain embodiments, an in vitro method of inhibiting gene expression is provided comprising contacting one or more cells or a tissue with an oligomeric compound as provided herein.

In certain embodiments, oligomeric compounds are provided for use in an in vivo method of inhibiting gene expression comprising contacting one or more cells, a tissue or an animal with the oligomeric compound.

In certain embodiments, oligomeric compounds are provided for use in medical therapy.

DETAILED DESCRIPTION OF THE INVENTION

Provided herein are oligomeric compounds having at least one monomer subunit having Formula III, compounds having Formula I useful for making certain of the oligomeric compounds and methods of using the oligomeric compounds. In certain embodiments, the oligomeric compounds provided herein are useful for modulating the activity of a target nucleic acid. In certain embodiments, the morpholino modified oligomeric compounds provided herein provide an improved toxicity profile compared to an otherwise unmodified oligomeric compound.

In certain embodiments, oligomeric compounds are provided having at least one monomer subunit having Formula III, compounds having Formula I useful for making the oligomeric compounds and methods of using the oligomeric compounds.

In certain embodiments, oligomeric compounds are provided comprising from 10 to 30 monomer subunits wherein at least one monomer subunit has Formula III:

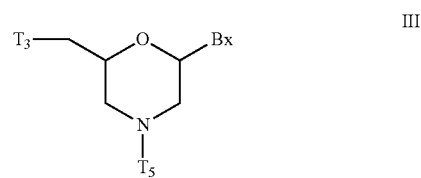

wherein independently for each monomer subunit having Formula III:

Bx is an optionally protected heterocyclic base moiety;

$T_3$ is hydroxyl, a protected hydroxyl, an internucleoside linking group linking the monomer subunit of Formula III to the 5'-remainder of the oligomeric compound or a terminal group;

$T_5$ is H, $C_{1-6}$ alkyl, a terminal group or a nitrogen protecting group when located on the 3'-terminus of the oligomeric compound wherein at least one $T_5$ is a linking group having the formula:

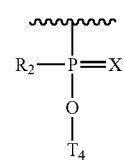

wherein independently for each $T_5$:

$R_2$ is hydroxyl, $C_{1-6}$ alkyl or substituted $C_{1-6}$ alkyl comprising an optionally protected substituent group selected from halogen, $OJ_1$, $NJ_1J_2$, $SJ_1$, $N_3$, $OC(=Q)J_1$, $OC(=Q)NJ_1J_2$, $NJ_3C(=Q)NJ_1J_2$ and CN, wherein each $J_1$, $J_2$ and $J_3$ is, independently, H or $C_1$-$C_6$ alkyl, and Q is O, S or $NJ_1$;

X is O or S wherein when X is O, at least one $R_2$ is other than hydroxyl; and $T_4$ is a single bond connecting said linking group to the 3'-remainder of the oligomeric compound or $T_4$ forms a single bond with a $T_3$ from a second monomer subunit having Formula III In certain embodiments, X is O and $R_2$ is OH and the oligomeric compound is other than an siRNA.

In certain embodiments, gapped oligomeric compounds are provided consisting of from 2 to 5 monomer subunits, a second region consisting of from 2 to 5 monomer subunits and a gap region located between the first and second region consisting of from 8 to 12 monomer subunits wherein each monomer subunit in the first and second region is a modified nucleoside and each monomer subunit in the gap region is an unmodified nucleoside or a modified nucleoside different from the modified nucleosides in the first and second region and wherein at least one of the monomer subunits has Formula II.

In certain embodiments, gapped oligomeric compounds as provided herein are described by the shorthand $E_5/G/E_3$ wherein the "$E_5$" is the external region at the 5'-end, "G" is the gap region and "$E_3$" is the external region at the 3'-end. In certain embodiments, gapped oligomeric compounds are provided comprising a 2/10/2 motif. In certain embodiments, gapped oligomeric compounds are provided comprising a 3/10/3 motif. In certain embodiments, gapped oligomeric compounds are provided comprising a 5/10/5 motif. In certain embodiments, the modified nucleosides in the external regions are bicyclic modified nucleosides. In certain embodiments, the modified nucleosides in the external regions each comprise a 2'-substituent group selected from F, $OCH_3$, $O(CH_2)_2$—$OCH_3$ and $OCH_2C(=O)$—$N(H)CH_3$. In certain embodiments, the modified nucleosides in the external regions are a mixture of bicyclic modified nucleosides and modified nucleosides comprising at least one substituent group. In certain embodiments, the modified nucleosides in the external regions are a mixture of bicyclic modified nucleosides comprising a bridging group selected from 4'-$CH_2$—O-2', 4'-$(CH_2)_2$—O-2', 4'-$CH(CH_3)$—O-2', 4'-$CH_2$—$N(CH_3)$—O-2', 4'-$CH_2$—$C(H)(CH_3)$-2' and 4'-$CH_2$—$C(=CH_2)$-2' and modified nucleosides comprising a 2'-substituent group selected from F, $OCH_3$, $O(CH_2)_2$—$OCH_3$ and $OCH_2C(=O)$—$N(H)CH_3$. In certain embodiments, the modified nucleosides in the external regions are a mixture of bicyclic modified nucleosides comprising a bridging group selected from 4'-$CH_2$—O-2' or 4'-CH[(S)—$(CH_3)$]—O-2' and modified nucleosides comprising a 2'-substituent group selected from F, $OCH_3$, $O(CH_2)_2$—$OCH_3$ and $OCH_2C(=O)$—$N(H)CH_3$. In certain embodiments, the modified nucleosides in the external regions are a mixture of bicyclic modified nucleosides comprising a bridging group selected from 4'-CH[(S)—$(CH_3)$]—O-2' and modified nucleosides comprising a 2'-$O(CH_2)_2$—$OCH_3$ substituent group. In certain embodiments, each modified nucleoside in each external region is a bicyclic modified nucleoside comprising a 4'-CH[(S)—$(CH_3)$]—O-2' bridging group. In certain embodiments, each modified nucleoside in each external region is a 2'-$O(CH_2)_2$—$OCH_3$ modified nucleoside. In certain embodiments, the gapped oligomeric compound is further functionalized by addition of a conjugate group.

In certain embodiments, oligomeric compounds are provided comprising from 12 to 28 monomer subunits comprising at least one $T(Z_aT_b)_cZ_d$ motif where each a and b is, independently, from 1 to about 8, c is from 1 to about 12, d is 0 or 1, one of T and Z is a β-D-2'-deoxyribonucleoside and the other of T and Z is a monomer subunit having Formula III:

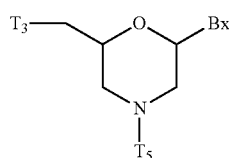

III wherein independently for each monomer subunit having Formula III:
Bx is an optionally protected heterocyclic base moiety;
$T_3$ is hydroxyl, a protected hydroxyl, an internucleoside linking group linking the monomer subunit of Formula III to the 5'-remainder of the oligomeric compound or a terminal group;

$T_5$ is H, $C_{1-6}$ alkyl, a nitrogen protecting or a linking group having the formula:

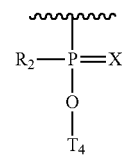

wherein independently for each $T_5$:
$R_2$ is hydroxyl, $C_{1-6}$ alkyl or substituted $C_{1-6}$ alkyl comprising an optionally protected substituent group selected from halogen, $OJ_1$, $NJ_1J_2$, $SJ_1$, $N_3$, $OC(=Q)J_1$, $OC(=Q)NJ_1J_2$, $NJ_3C(=Q)NJ_1J_2$ and CN, wherein each $J_1$, $J_2$ and $J_3$ is, independently, H or $C_1$-$C_6$ alkyl, and Q is O, S or $NJ_1$;
X is O or S; and
$T_4$ is a single bond connecting said linking group to the 3'-remainder of the oligomeric compound or $T_4$ forms a single bond with a $T_3$ from a second monomer subunit having Formula III.

In certain embodiments, compounds having reactive phosphorus groups are provided that are useful for preparing oligomeric compounds of the invention on an automated synthesizer. In certain embodiments, compounds having reactive phosphorus groups are provided having Formula I:

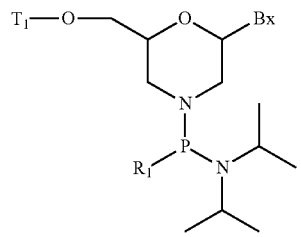

wherein:
Bx is an optionally modified heterocyclic base moiety;
$T_1$ is H or a hydroxyl protecting group; and
$R_1$ is $C_{1-6}$ alkyl or substituted $C_{1-6}$ alkyl comprising an optionally protected substituent group selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$. In certain embodiments, $R_1$ is alkyl such as methyl. In certain embodiments, $R_1$ is substituted alkyl such as alkoxy substituted alkyl. In certain embodiments, $R_1$ is $CH_3O(CH_2)_3$—.

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Where permitted, all patents, applications, published applications and other publications and other data referred to throughout in the disclosure are incorporated by reference herein in their entirety.

Unless otherwise indicated, the following terms have the following meanings:

As used herein, "2'-deoxynucleoside" means a nucleoside comprising 2'-H(H) furanosyl sugar moiety, as found in naturally occurring deoxyribonucleic acids such as a β-D-2'-deoxyribnucleoside (DNA). In certain embodiments, a 2'-deoxynucleoside may comprise a modified nucleobase or may comprise an RNA nucleobase (uracil).

As used herein, "2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

As used herein, "Antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound. In certain embodiments, antisense activity is a change in splicing of a pre-mRNA nucleic acid target. In certain embodiments, antisense activity is an increase in the amount or expression of a target nucleic acid or protein encoded by such target nucleic acid compared to target nucleic acid levels or target protein levels in the absence of the antisense compound.

As used herein, "Antisense compound" means a compound comprising an antisense oligonucleotide and optionally one or more additional features, such as a conjugate group or terminal group.

As used herein, "Antisense oligonucleotide" means an oligonucleotide that (1) has a nucleobase sequence that is at least partially complementary to a target nucleic acid and that (2) is capable of producing an antisense activity in a cell or animal.

As used herein, "Ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom.

As used herein, "Bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge or bridging group connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

As used herein, "Cell-targeting moiety" means a conjugate group or portion of a conjugate group that is capable of binding to a particular cell type or particular cell types.

As used herein, "Cleavable moiety" means a bond or group of atoms that is cleaved under physiological conditions, for example, inside a cell, an animal, or a human.

As used herein, "Complementary" in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include, but unless otherwise specific are not limited to, adenine (A) and thymine (T), adenine (A) and uracil (U), cytosine (C) and guanine (G), 5-methyl cytosine ($^m$C) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide.

As used herein, "Conjugate group" means a group of atoms that is directly or indirectly attached to an oligonucleotide. Conjugate groups include a conjugate group and a conjugate linker that attaches the conjugate group to the oligonucleotide wherein the attachment may include a cleavable moiety.

As used herein, "Conjugate linker" means a group of atoms comprising at least one bond that connects a conjugate group to an oligonucleotide wherein the attachment may include a cleavable moiety.

As used herein, "Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "Duplex" means two oligomeric compounds that are paired. In certain embodiments, the two oligomeric compounds are paired via hybridization of complementary nucleobases.

As used herein, "Extra-hepatic cell type" means a cell type that is not a hepatocyte.

As used herein, "Extra-hepatic nucleic acid target" means a target nucleic acid that is expressed in tissues other than liver. In certain embodiments, extra-hepatic nucleic acid targets are not expressed in the liver or not expressed in the liver at a significant level. In certain embodiments, extra-hepatic nucleic acid targets are expressed outside the liver and also in the liver.

As used herein, "Extra-hepatic tissue" means a tissue other than liver.

As used herein, "Fully modified" in reference to a modified oligonucleotide means a modified oligonucleotide in which each sugar moiety is modified. "Uniformly modified" in reference to a modified oligonucleotide means a fully modified oligonucleotide in which each sugar moiety is the same. For example, the nucleosides of a uniformly modified oligonucleotide can each have a 2'-MOE modification but different nucleobase modifications, and the internucleoside linkages may be different.

As used herein, "Gapmer" means an antisense oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

As used herein, "Hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "Inhibiting the expression or activity" refers to a reduction or blockade of the expression or activity relative to the expression of activity in an untreated or control sample and does not necessarily indicate a total elimination of expression or activity.

As used herein, "Internucleoside linkage" or "internucleoside linking group" means a group or bond that forms a covalent linkage between adjacent nucleosides in an oligonucleotide. As used herein "modified internucleoside linkage" means any internucleoside linkage other than a naturally occurring, phosphate internucleoside linkage. Non-phosphodiester linkages are referred to herein as modified internucleoside linkages. "Phosphorothioate linkage" means a modified phosphodiester linkage in which one of the non-bridging oxygen atoms is replaced with a sulfur atom. A phosphorothioate internucleoside linkage is a modified internucleoside linkage. Modified internucleoside linkages include linkages that comprise abasic nucleosides. As used herein, "abasic nucleoside" means a sugar moiety in an oligonucleotide or oligomeric compound that is not directly connected to a nucleobase. In certain embodiments, an abasic nucleoside is adjacent to one or two nucleosides in an oligonucleotide.

As used herein, "Lipophilic group" or "lipophilic" in reference to a chemical group means a group of atoms that is more soluble in lipids or organic solvents than in water and/or has a higher affinity for lipids than for water. In certain embodiments, lipophilic groups comprise a lipid. As used herein "lipid" means a molecule that is not soluble in water or is less soluble in water than in organic solvents. In certain embodiments, compounds of the present invention comprise lipids selected from saturated or unsaturated fatty acids, steroids, fat soluble vitamins, phospholipids, sphingolipids, hydrocarbons, mono-, di-, and tri-glycerides, and synthetic derivatives thereof.

As used herein the term "monomer subunit" is meant to include all manner of monomers that are amenable to oligomer synthesis. In general a monomer subunit includes at least a sugar moiety or modified sugar moiety having at least two reactive sites that can form linkages to further monomer subunits. Essentially all monomer subunits include a nucleobase that is hybridizable to a complementary site on a nucleic acid target. Reactive sites on monomer subunits located on the termini of an oligomeric compound can be protected or unprotected (generally OH) or can form an attachment to a terminal group (conjugate or other group). Monomer subunits include, without limitation, nucleosides and modified nucleosides. In certain embodiments, monomer subunits include nucleosides such as β-D-ribonucleosides and β-D-2'-deoxyribonucleosides and modified nucleosides including but not limited to substituted nucleosides (such as 2', 5' and bis substituted nucleosides), 4'-S-modified nucleosides (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—CHR$_a$-4' bridging group, wherein R$_a$ is H, alkyl or substituted alkyl), other modified nucleosides and nucleosides having sugar surrogates.

As used herein, "Non-bicyclic modified sugar" or "non-bicyclic modified sugar moiety" means a modified sugar moiety that comprises a modification, such as a substituent, that does not form a bridge between two atoms of the sugar to form a second ring.

As used herein, "Linked nucleosides" are nucleosides that are connected in a continuous sequence (i.e. no additional nucleosides are present between those that are linked).

As used herein, "Mismatch" or "non-complementary" means a nucleobase of a first oligonucleotide that is not complementary with the corresponding nucleobase of a second oligonucleotide or target nucleic acid when the first and second oligomeric compound are aligned.

As used herein, "MOE" means methoxyethoxy. "2'-MOE" means a —OCH$_2$CH$_2$OCH$_3$ group at the 2' position of a furanosyl ring.

As used herein, "Motif" means the pattern of unmodified and/or modified sugar moieties, nucleobases, and/or internucleoside linkages, in an oligonucleotide.

As used herein, "Multi-tissue disease or condition" means a disease or condition affects or is effected by more than one tissue. In treating a multi-tissue disease or condition, it is desirable to affect more than one tissue type. In certain embodiments, treatment of disease or condition may be enhanced by treating the disease or condition in multiple tissues. For example, in certain embodiments, a disease or condition may manifest itself in the liver tissue and the muscle tissue. In certain embodiments, treating the disease or condition in the liver tissue and the muscle tissue will be more effective than treating the disease in either the liver tissue or the muscle tissue.

As used herein, "Naturally occurring" means found in nature.

As used herein, "Nucleobase" means an unmodified nucleobase or a modified nucleobase. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one unmodified nucleobase. Oligomeric compounds are most often prepared having nucleobases selected from adenine, guanine, thymine, cytosine, 5'-methyl cytosine and uracil. The optionally protected nucleobases commonly used for the synthesis of oligomeric compounds are 6-N-benzoyladenine, 2-N-isobutyrylguanine, 4-N-benzoylcytosine, 5'-methyl-4-N-benzoylcytosine, thymine and uracil.

As used herein, "Nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase.

As used herein, "Oligomeric compound" means a compound consisting of an oligonucleotide and optionally one or more additional features, such as a conjugate group or other terminal group.

As used herein, "Oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "Pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water; sterile saline; or sterile buffer solution.

As used herein, "Pharmaceutically acceptable salts" means physiologically and pharmaceutically acceptable salts of compounds, such as oligomeric compounds, i.e., salts that retain the desired biological activity of the parent compound and do not impart undesired toxicological effects thereto.

As used herein, "Pharmaceutical composition" means a mixture of substances suitable for administering to a subject. For example, a pharmaceutical composition may comprise an antisense compound and a sterile aqueous solution. In certain embodiments, a pharmaceutical composition shows activity in free uptake assay in certain cell lines.

As used herein, "Phosphorus moiety" means a group of atoms comprising a phosphorus atom. In certain embodiments, a phosphorus moiety comprises a mono-, di-, or tri-phosphate, or phosphorothioate.

As used herein, "Prodrug" means a therapeutic agent in a form outside the body that is converted to a different form within the body or cells thereof. Typically conversion of a prodrug within the body is facilitated by the action of an enzymes (e.g., endogenous or viral enzyme) or chemicals present in cells or tissues and/or by physiologic conditions.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense oligonucleotides that act through RNase H.

As used herein, "RNA-like nucleoside" means a modified nucleoside other than a β-D-ribose nucleoside that provides an A-form (northern) duplex when incorporated into an oligomeric compound and duplexed with a complementary RNA. RNA-like nucleosides are used as replacements for RNA nucleosides in oligomeric compounds to enhance one or more properties such as, for example, nuclease resistance and or hybridization affinity. RNA-like nucleosides include, but are not limited to modified furanosyl nucleosides that adopt a 3'-endo conformational geometry when put into an oligomeric compound. RNA-like nucleosides also include RNA surrogates such as F-HNA. RNA-like nucleosides include but are not limited to modified nucleosides comprising a 2'-substituent group selected from F, $O(CH_2)_2OCH_3$ (MOE) and $OCH_3$. RNA-like nucleosides also include but are not limited to modified nucleosides comprising bicyclic furanosyl sugar moiety comprising a 4'-$CH_2$—O-2', 4'-$(CH_2)_2$—O-2', 4'-C(H)[(R)—$CH_3$]—O-2' or 4'—C(H)[(S)—$CH_3$]—O-2' bridging group.

As used herein, "Single-stranded" in reference to an oligomeric compound means such a compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex, in which case it would no longer be single-stranded.

As used herein, "Sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars. As used herein, "sugar surrogate" or means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "Target nucleic acid" means a naturally occurring, identified nucleic acid. In certain embodiments, target nucleic acids are endogenous cellular nucleic acids, including, but not limited to RNA transcripts, pre-mRNA, mRNA, microRNA. In certain embodiments, target nucleic acids are viral nucleic acids. In certain embodiments, target nucleic acids are nucleic acids that an antisense compound is designed to affect.

As used herein, "Target region" means a portion of a target nucleic acid to which an antisense compound is designed to hybridize.

In certain embodiments, the oligomeric compounds as provided herein can be modified by covalent attachment of one or more terminal groups to the 5' or 3'-terminal groups. A terminal group can also be attached at any other position at one of the terminal ends of the oligomeric compound. As used herein the terms "5'-terminal group", "3'-terminal group", "terminal group" and combinations thereof are meant to include useful groups known to the art skilled that can be placed on one or both of the terminal ends, including but not limited to the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

I. Certain Oligonucleotides

In certain embodiments, the invention provides oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836).

In certain embodiments, a 2'-substituted nucleoside or 2'-non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a non-bridging 2'-substituent group selected from: F, OCH$_3$, and OCH$_2$CH$_2$OCH$_3$.

Nucleosides comprising modified sugar moieties, such as non-bicyclic modified sugar moieties, may be referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., J. Org. Chem., 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)- 2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Wengel et a., U.S. Pat. No. 7,053,207; Imanishi et al., U.S. Pat. No. 6,268,490; Imanishi et al., U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

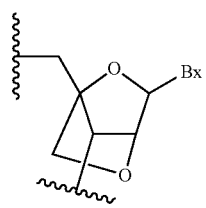

LNA (β-D-configuration)
bridge = 4'-CH$_2$—O-2'

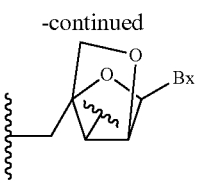

α-L-LNA (α-L-configuration)
bridge = 4'-CH$_2$—O-2'

α-L-methyleneoxy (4'-CH$_2$—O-2') or α-L-LNA bicyclic nucleosides have been incorporated into antisense oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, CJ. *Bioorg. & Med. Chem.* 2002, 10, 841-854), fluoro HNA:

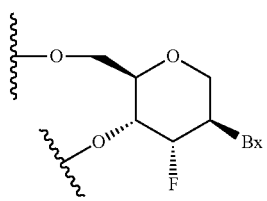

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

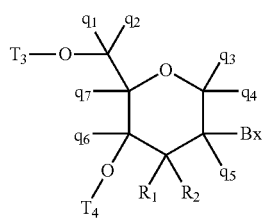

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

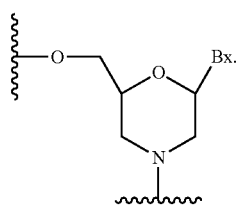

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

1. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($-C\equiv C-CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No.

5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

B. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—$CH_2$—$N(CH_3)$—O—$CH_2$—), thiodiester, thionocarbamate (—O—C(=O)(NH)—S—); siloxane (—O—$SiH_2$—O—); and N,N'-dimethylhydrazine (—$CH_2$—$N(CH_3)$—$N(CH_3)$—). Modified internucleoside linkages, compared to naturally occurring phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-$CH_2$—$N(CH_3)$—O-5'), amide-3 (3'-$CH_2$—C(=O)—N(H)-5'), amide-4 (3'—$CH_2$—N(H)—C(=O)-5'), formacetal (3'-O—$CH_2$—O-5'), methoxypropyl, and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

C. Certain Motifs

In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxynucleoside.

In certain embodiments, the gapmer is a deoxy gapmer. In such embodiments, the nucleosides on the gap side of each wing/gap junction are unmodified 2'-deoxynucleosides and the nucleosides on the wing sides of each wing/gap junction are modified nucleosides. In certain such embodiments, each nucleoside of the gap is an unmodified 2'-deoxynucleoside. In certain such embodiments, each nucleoside of each wing is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain such embodiments, each nucleoside to the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified oligonucleotide comprises the same 2'-modification.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments, the block is within 3 nucleosides of the 3'-end of the oligonucleotide. In certain embodiments, the block is at the 5'-end of the oligonucleotide. In certain embodiments, the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are phosphodiester linkages. In certain embodiments, the terminal internucleoside linkages are modified.

D. Certain Lengths

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides E. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a region of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists if of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 90%, at least 95%, or 100% complementary to the second oligonucleotide or nucleic acid, such as a target nucleic acid.

II. Certain Oligomeric Compounds

In certain embodiments, the invention provides oligomeric compounds, which consist of an oligonucleotide (modified or unmodified) and optionally one or more terminal groups such as a conjugate group. Conjugate groups consist of one or more conjugate group and a conjugate linking group which links the conjugate group to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or other terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, abasic nucleosides, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., *Proc. Natl. Acad. Sci. USA*, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain oligomeric compounds, a conjugate moiety is attached to an oligonucleotide via a more complex conjugate linker comprising one or more conjugate linker moieties, which are sub-units making up a conjugate linker. In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments, such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methyl-cytosine, adenine, 6-N-benzoyladenine, guanine and 2-N-isobutyrylguanine. In certain embodiments, a cleavable moiety is an unprotected β-D-2'-deoxyribonucleoside nucleoside selected from uracil, thymine, cytosine, adenine and guanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds. In certain embodiments, linker nucleosides are located at the 5'-terminus of the oligomeric compound. In certain embodiments, linker nucleosides are located at the 3'-terminus of the oligomeric compound.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester —O—P(=O)(—OH)O—, a phosphate ester —O—P(=O)(—OH)$_2$, a carbamate, disulfide or a linkage comprising any phosphorus moiety such as —P(=O)(—OH)—. In certain embodiments, a cleavable bond is one or both of the esters of a phosphodiester. In certain embodiments, a cleavable moiety comprises a phosphate or phosphodiester. In certain embodiments, the cleavable moiety is a phosphodiester linkage between an oligonucleotide and a conjugate moiety or conjugate group. In certain embodiments, the cleavable moiety is a phosphodiester linkage between an oligonucleotide and a conjugate linker attaching a conjugate group. In certain embodiments, the cleavable moiety is a phosphodiester linkage between an oligonucleotide and a conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine. In certain embodiments, the cleavable moiety is from one to three nucleosides selected from 2'-deoxyadenosine 2'-deoxythymidine and 2'-deoxycytidine.

In certain embodiments, the conjugate group comprises a conjugate linker including a cleavable moiety having one of the formulas:

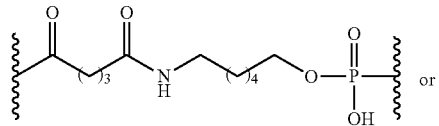 or

-continued

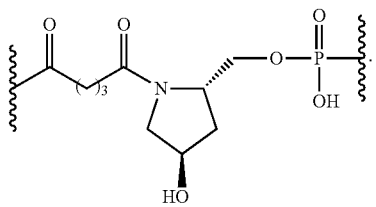

Wherein the phosphate group attaches the conjugate group to the gapped oligomeric compound. In certain embodiments, the phosphate group attaches the conjugate group to the 5'-terminal oxygen atom of the oligomeric compound. In certain embodiments, the phosphate group attaches the conjugate group to the 3'-terminal oxygen atom of the oligomeric compound.

3. Certain Cell-Targeting Conjugate Moieties

In certain embodiments, a conjugate group comprises a cell-targeting conjugate moiety. In certain embodiments, a conjugate group has the general formula:

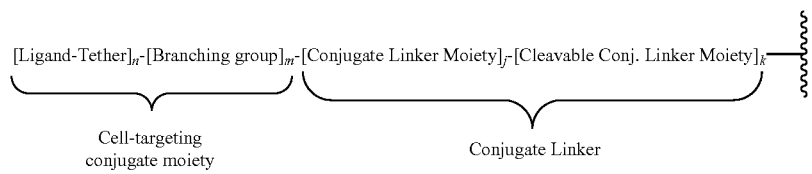

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0.

In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amide, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl, amide and oxo, in any combination. In certain embodiments, each tether is a linear aliphatic group comprising one or more groups selected from alkyl and amide, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian liver cell. In certain embodiments, each ligand has an affinity for the hepatic asialoglycoprotein receptor (ASGP-R). In certain embodiments, each ligand is a carbohydrate. In certain embodiments, each ligand is, independently selected from galactose, N-acetyl galactoseamine (GalNAc), mannose, glucose, glucoseamine and fucose. In certain embodiments, each ligand is N-acetyl galactoseam ine (GalNAc). In certain embodiments, the cell-targeting moiety comprises 3 GalNAc ligands. In certain embodiments, the cell-targeting moiety comprises 2 GalNAc ligands. In certain embodiments, the cell-targeting moiety comprises 1 GalNAc ligand.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," *Bioconjugate Chemistry,* 2003, 14, 18-29 or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, 47, 5798-5808). In certain such embodiments, each ligand is an amino sugar or a thio sugar. For example, amino sugars may be selected from any number of compounds known in the art, such as sialic acid, α-D-galactosamine, β-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, conjugate groups comprise a cell-targeting moiety having the formula:

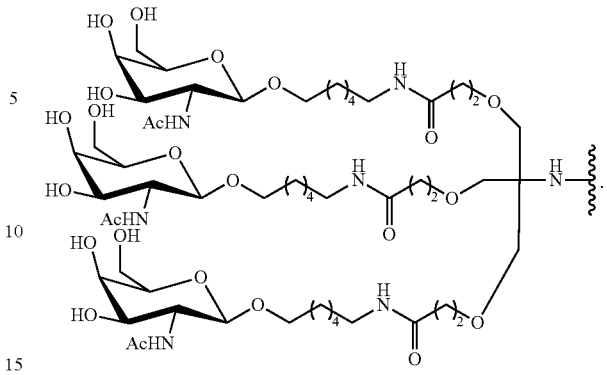

In certain embodiments, conjugate groups comprise a cell-targeting moiety having the formula:

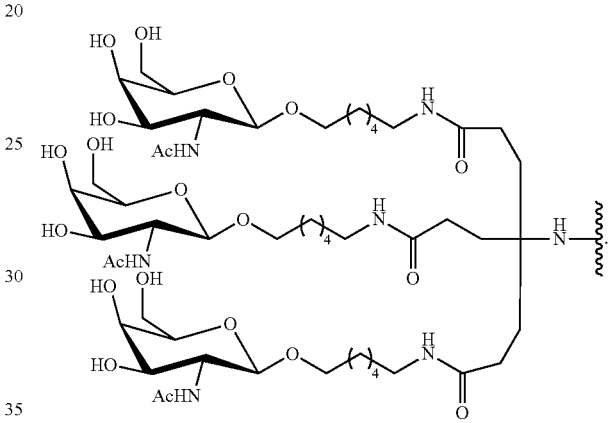

In certain embodiments, conjugate groups comprise a cell-targeting moiety having the formula:

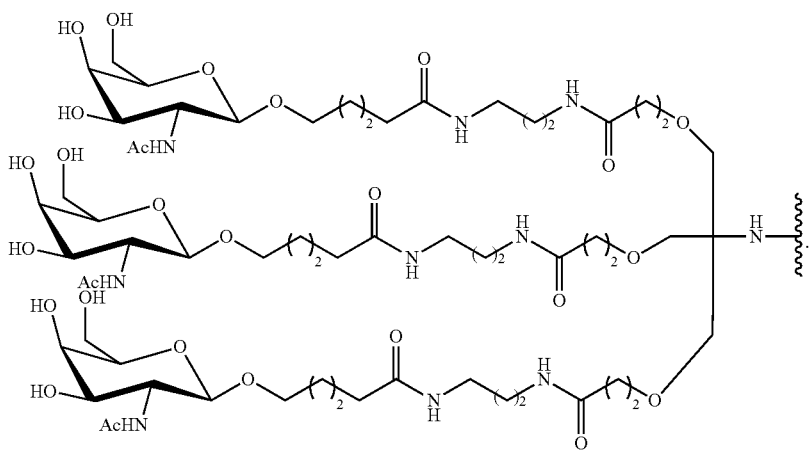

In certain embodiments, the conjugate group is attached to the 5'position of the oligomeric compound having the formula:

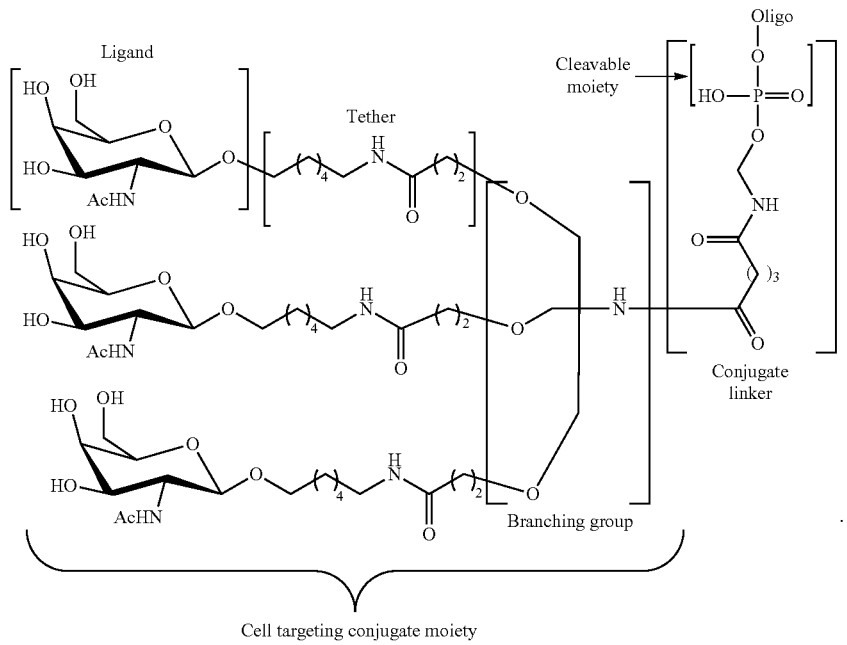

In certain embodiments, the conjugate group is attached to the 3'position of the oligomeric compound having the formula:

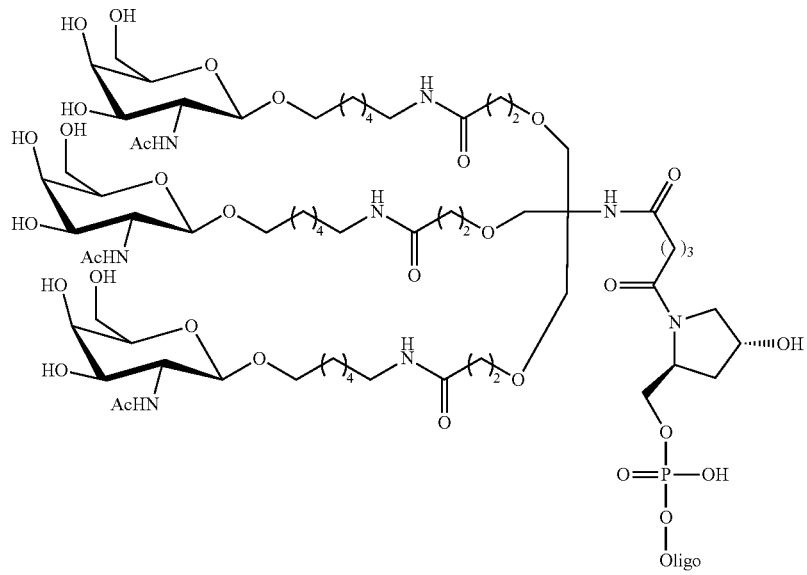

Representative United States patents, United States patent application publications, international patent application publications, and other publications that teach the preparation of certain of the above noted conjugate groups, oligomeric compounds comprising conjugate groups, tethers, conjugate linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/0148740, US 2011/0123520, WO 2013/033230 and WO 2012/037254, Biessen et al., *J. Med Chem.* 1995, 38, 1846-1852, Lee et al., *Bioorganic & Medicinal Chemistry* 2011, 19, 2494-2500, Rensen et al., *J. Biol. Chem.* 2001, 276, 37577-37584, Rensen et al., *J. Med Chem.* 2004, 47, 5798-5808, Sliedregt et al., *J. Med Chem.* 1999, 42, 609-618, and Valentijn et al., *Tetrahedron,* 1997, 53, 759-770.

In certain embodiments, oligomeric compounds comprise modified oligonucleotides comprising a gapmer and a conjugate group comprising at least one, two, or three GalNAc ligands. In certain embodiments antisense compounds and oligomeric compounds comprise a conjugate group found in any of the following references: Lee, *Carbohydrate*

Research, 1978, 67, 509-514; Connolly et al., *J Biol Chem*, 1982, 257, 939-945; Pavia et al., *Int J Pep Protein Res*, 1983, 22, 539-548; Lee et al., *Biochem*, 1984, 23, 4255-4261; Lee et al., *Glycoconjugate J*, 1987, 4, 317-328; Toyokuni et al., *Tetrahedron Lett*, 1990, 31, 2673-2676; Biessen et al., *J Med Chem*, 1995, 38, 1538-1546; Valentijn et al., *Tetrahedron*, 1997, 53, 759-770; Kim et al., *Tetrahedron Lett*, 1997, 38, 3487-3490; Lee et al., *Bioconjug Chem*, 1997, 8, 762-765; Kato et al., *Glycobiol*, 2001, 11, 821-829; Rensen et al., *J Biol Chem*, 2001, 276, 37577-37584; Lee et al., *Methods Enzymol*, 2003, 362, 38-43; Westerlind et al., *Glycoconj J*, 2004, 21, 227-241; Lee et al., *BioorgMed Chem Lett*, 2006, 16(19), 5132-5135; Maierhofer et al., *BioorgMed Chem*, 2007, 15, 7661-7676; Khorev et al., *BioorgMed Chem*, 2008, 16, 5216-5231; Lee et al., *BioorgMed Chem*, 2011, 19, 2494-2500; Kornilova et al., *Analyt Biochem*, 2012, 425, 43-46; Pujol et al., *Angew Chemie IntEdEngl*, 2012, 51, 7445-7448; Biessen et al., *J Med Chem*, 1995, 38, 1846-1852; Sliedregt et al., *J Med Chem*, 1999, 42, 609-618; Rensen et al., *J Med Chem*, 2004, 47, 5798-5808; Rensen et al., *Arterioscler Thromb Vasc Biol*, 2006, 26, 169-175; van Rossenberg et al., *Gene Ther*, 2004, 11, 457-464; Sato et al., *J Am Chem Soc*, 2004, 126, 14013-14022; Lee et al., *J Org Chem*, 2012, 77, 7564-7571; Biessen et al., *FASEB J*, 2000, 14, 1784-1792; Rajur et al., *Bioconjug Chem*, 1997, 8, 935-940; Duff et al., *Methods Enzymol*, 2000, 313, 297-321; Maier et al., *Bioconjug Chem*, 2003, 14, 18-29; Jayaprakash et al., *Org Lett*, 2010, 12, 5410-5413; Manoharan, Antisense Nucleic AcidDrugDev, 2002, 12, 103-128; Merwin et al., *Bioconjug Chem*, 1994, 5, 612-620; Tomiya et al., *Bioorg Med Chem*, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132.

In certain embodiments, compounds of the invention are single-stranded. In certain embodiments, oligomeric compounds are paired with a second oligonucleotide or oligomeric compound to form a duplex, which is double-stranded.

III. Certain Antisense Compounds

In certain embodiments, the present invention provides antisense compounds, which comprise or consist of an oligomeric compound comprising an antisense oligonucleotide, having a nucleobase sequences complementary to that of a target nucleic acid. In certain embodiments, antisense compounds are single-stranded. Such single-stranded antisense compounds typically comprise or consist of an oligomeric compound that comprises or consists of a modified oligonucleotide and optionally a conjugate group. In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

In certain embodiments, oligomeric compounds of antisense compounds are capable of hybridizing to a target nucleic acid, resulting in at least one antisense activity. In certain embodiments, antisense compounds selectively affect one or more target nucleic acid. Such selective antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, the invention provides antisense compounds that are sufficiently "DNA-like" to elicit RNase H activity. Further, in certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, compounds comprising oligonucleotides having a gapmer nucleoside motif including one or more modified internucleoside linkages, having one of formulas I to XVI as described herein, have desirable properties compared to otherwise equivalent gapmers. In certain circumstances, it is desirable to identify gapmer motifs resulting in a favorable combination of potent antisense activity and relatively low toxicity. In certain embodiments, gapped oligomeric compounds of the present invention have a favorable therapeutic index (measure of potency divided by measure of toxicity).

In certain embodiments, hybridization of an antisense compound to a target nucleic acid does not result in recruitment of a protein that cleaves that target nucleic acid. In certain such embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain such embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

IV. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism (SNP). In certain such embodiments, the antisense compound is capable of modulating expression of one allele of the SNP-containing target nucleic acid to a greater or lesser extent than it modulates another allele. In certain embodiments, an antisense compound hybridizes to a (SNP)-containing target nucleic acid at the single-nucleotide polymorphism site.

In certain embodiments, antisense compounds are at least partially complementary to more than one target nucleic acid. For example, antisense compounds of the present invention may mimic microRNAs, which typically bind to multiple targets.

A. Complementarity/Mismatches to the Target Nucleic Acid

In certain embodiments, antisense compounds comprise antisense oligonucleotides that are complementary to the target nucleic acid over the entire length of the oligonucleotide. In certain embodiments, such oligonucleotides are 99% complementary to the target nucleic acid. In certain embodiments, such oligonucleotides are 95% complementary to the target nucleic acid. In certain embodiments, such oligonucleotides are 90% complementary to the target nucleic acid. In certain embodiments, such oligonucleotides are 85% complementary to the target nucleic acid. In certain embodiments, such oligonucleotides are 80% complementary to the target nucleic acid. In certain embodiments, antisense oligonucleotides are at least 80% complementary to the target nucleic acid over the entire length of the oligonucleotide and comprise a region that is 100% or fully complementary to a target nucleic acid. In certain such embodiments, the region of full complementarity is from 6 to 20 nucleobases in length. In certain such embodiments, the region of full complementarity is from 10 to 18 nucleobases in length. In certain such embodiments, the region of full complementarity is from 18 to 20 nucleobases in length.

In certain embodiments, the oligomeric compounds of antisense compounds comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the antisense compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region (5'-gap junction). In certain such embodiments, the mismatch is at position 9, 8, 7, 6, 5, 4, 3, 2, 1 from the 3'-end of the gap region (3a'-gap junction). In certain such embodiments, the mismatch is at position 1, 2, 3, or 4 from the 5'-end of the wing region. In certain such embodiments, the mismatch is at position 4, 3, 2, or 1 from the 3'-end of the wing region.

B. Certain Target Nucleic Acids in Certain Tissues

In certain embodiments, antisense compounds comprise or consist of an oligonucleotide comprising a region that is complementary to a target nucleic acid, wherein the target nucleic acid is expressed in an extra-hepatic tissue. Extra-hepatic tissues include, but are not limited to: skeletal muscle, cardiac muscle, smooth muscle, adipose, white adipose, spleen, bone, intestine, adrenal, testes, ovary, pancreas, pituitary, prostate, skin, uterus, bladder, brain, glomerulus, distal tubular epithelium, breast, lung, heart, kidney, ganglion, frontal cortex, spinal cord, trigeminal ganglia, sciatic nerve, dorsal root ganglion, epididymal fat, diaphragm, pancreas, and colon.

V. Certain Pharmaceutical Compositions

In certain embodiments, the present invention provides pharmaceutical compositions comprising one or more antisense compound or a salt thereof. In certain such embodiments, the pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one antisense compound and sterile water. In certain embodiments, the sterile water is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile PBS. In certain embodiments, the sterile PBS is pharmaceutical grade PBS.

In certain embodiments, pharmaceutical compositions comprise one or more or antisense compound and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an antisense compound encompass any pharmaceutically acceptable salts of the antisense compound, esters of the antisense compound, or salts of such esters. In certain embodiments, pharmaceutical compositions comprising antisense compounds comprising one or more antisense oligonucleotide, upon administration to an animal, including a human, are capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an antisense compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

Nonlimiting Disclosure and Incorporation by Reference

Each of the literature and patent publications listed herein is incorporated by reference in its entirety. While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$c indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Included in the compounds provided herein are all such possible isomers, including their racemic and optically pure forms, unless specified otherwise. Likewise, all cis- and trans-isomers and tautomeric forms are also included unless otherwise indicated. Unless otherwise indicated, compounds described herein are intended to include corresponding salt forms.

EXAMPLES

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. No. 5,256,775 or 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH$_4$OAc with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., *J. Biol. Chem.* 1991, 266(27), 18162-18171. Results obtained with HPLC-purified material are generally similar to those obtained with non-HPLC purified material.

Example 4

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus MgCl$_2$, 6.6 mM MgCl$_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/-extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10

RNA Isolation

Poly(A)+ mRNA Isolation

Poly(A)+ mRNA is isolated according to Miura et al., (Clin. Chem., 1996, 42, 1758-1764). Other methods for poly(A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
Forward primer:
                                        (SEQ ID NO: 2)
AATGGCTAAGTGAAGATGACAATCAT.

Reverse primer:
                                        (SEQ ID NO: 3)
TGCACATATCATTACACCAGTTCGT.
```

And the PCR probe:

FAM-TTGCAGCAATTCACTGTAAAGCTG-GAAAGG-TAMRA (SEQ ID NO: 4), where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µL/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

General Procedure for Synthesis of DMT Diamidite Morpholino Monomer, Compound 4

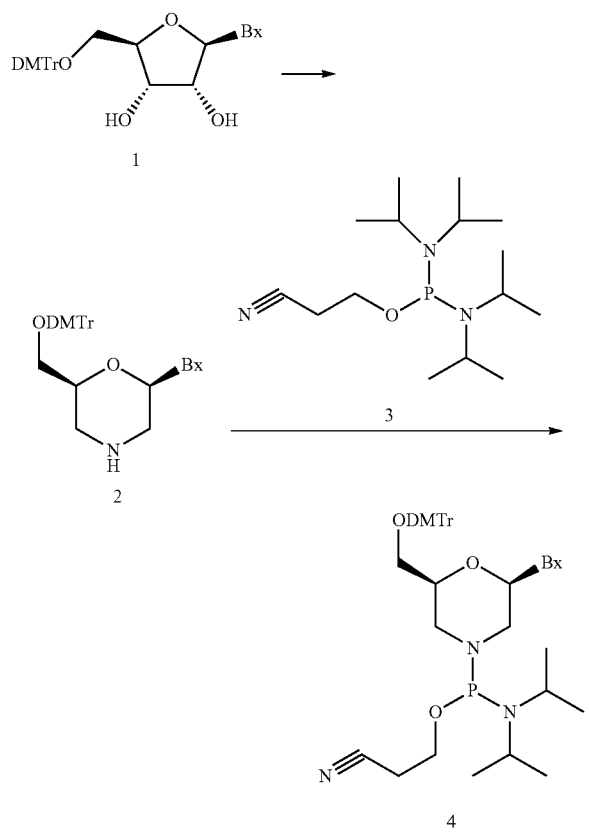

Wherein Bx is an optionally protected heterocyclic base moiety.

Compound 4 is prepared from commercially available compounds 1 and 3 as per published literature procedures (Caruthers et al., *J Am Chem Soc*, 2016, 138(48), 15663-15672).

Following these procedures Compound 4a (Bx=thymine) was prepared. $^1$H NMR was consistent with the structure.

Following these procedures compounds 4b-d are prepared (Compound 4b, Bx=5'-methyl-4-N-isobutyrylcytosine; Compound 4c, Bx=6-N-benzoyladenine; and Compound 4d, Bx=2-N-isobutyrylguanine).

Example 14

General Procedure for Synthesis of Compound 5

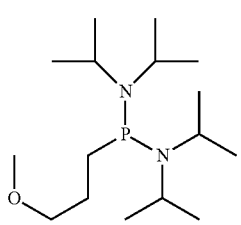

Compound 5 was prepared by suspending Mg (s, 4.18 g) in dry THF (150 mL) and 1-bromo-3-methoxypropane (12 mL) was added in portions over 20 minutes with periodic cooling in an ice bath to keep the temperature under 30° C. The reaction was then allowed to stir an additional 10 minutes at room temperature. The solution was then added to a second flask containing bis(diisopropylamino)chlorophosphine (25 grams) as a stirred cold suspension in dry diethyl ether. The reaction was allowed to come to room temperature and stirred for one hour. The reaction mixture was filtered through a plug of Celite, and the solids are rinsed with Et$_2$O. The filtrates are pooled, and the solvent were removed. The residue was suspended in dry ACN (75 ml) and transferred to a separatory funnel. The product was extracted with hexanes washed with additional ACN and concentrated to provide Compound 5, 27.10 g (84.1% yield) which was used in the next reaction immediately. $^{13}$P NMR was consistent with the structures.

Example 15

General Procedure for Synthesis of DMT Diamidite Morpholino Monomer Compound 6, Synthesis of Compounds 6a-d

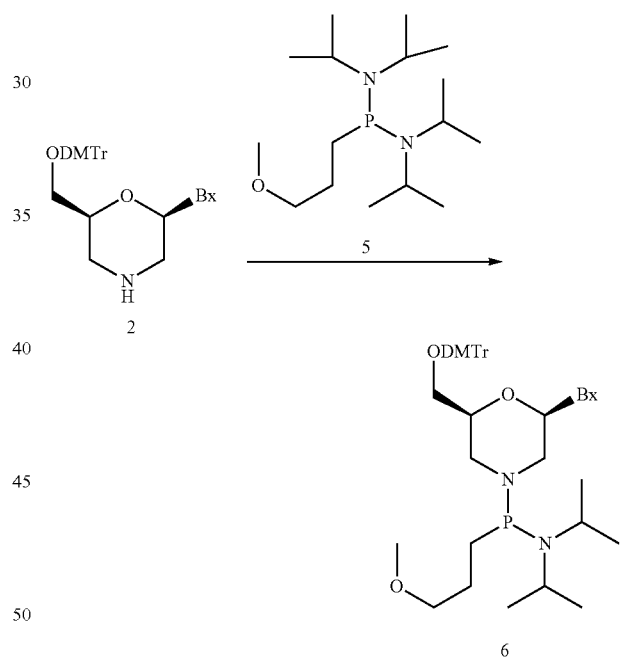

Compound 2 (1.84 mmoles, prepared as illustrated in Example 13) is treated with tetrazole (200 mg, 2.76 mmol, 1.5 equiv), 1-methyl imidazole (75 µL, 0.92 mmol, 0.5 equiv) and Compound 5 (1.5 equivalents, 840 mg, prepared as illustrated in Example 14) in dry DMF (18 mL) for 20 hours at room temperature under nitrogen. The reaction was diluted with EtOAc (50 ml) and washed with 1:1 H$_2$O and saturated NaHCO$_3$ (2×50 ml) followed by brine (1×50 ml). The organic layers are pooled, dried over MgSO$_4$, filtered, and concentrated. The crude material is purified by silica gel chromatography to give the final compound.

Following these procedures Compound 6a (Bx=thymine) was prepared in a 50% yield. $^1$H NMR was consistent with the structure.

Example 16

General Procedure for Synthesis of DMT Diamidite Morpholino Monomer Compound 8, Synthesis of Compounds 8a-d

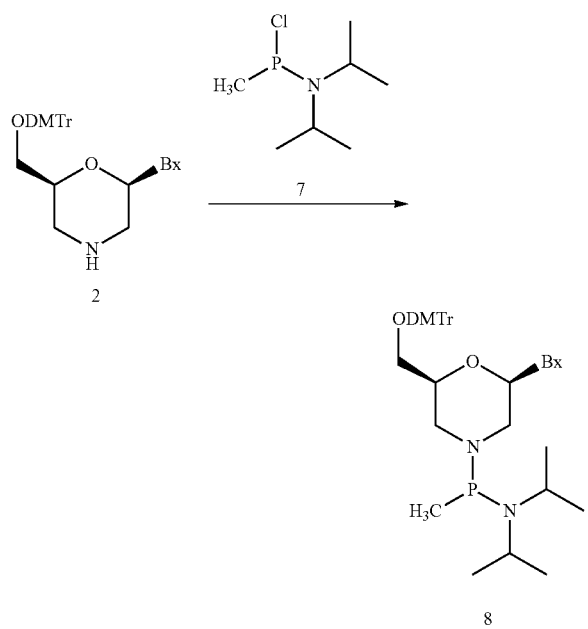

Compound 2 (18.9 mmoles, prepared as illustrated in Example 13) is treated with tetrazole (1.06 g), 1-methyl imidazole (665 µL) and Compound 7 (1.5 equivalents, commercially available from ChemGenes) in DMF (190 mL) for 20 hours at which time the solvent was removed under reduced pressure with the temperature maintained below 35° C. The residue is then diluted with EtOAc and washed with 1:1 $H_2O$ and brine followed by, $H_2O$, saturated $NaHCO_3$ and NaCl (sat). The organic layers are pooled, dried over $MgSO_4$, filtered, and concentrated. The crude material is purified by silica gel chromatography to give the final compound.

Following these procedures compounds 8a-d are prepared (Compound 8a, Bx=thymine; Compound 8b, Bx=5'-methyl-4-N-isobutyrylcytosine; Compound 8c, Bx=6-N-benzoyladenine; and Compound 8d, Bx=2-N-isobutyrylguanine).

Example 17

Morpholino Oligonucleotide Synthesis

Morpholino modified oligonucleotides were synthesized on a 2 µmol scale on an ABI 394 DNA/RNA synthesizer using polystyrene-based VIMAD Unylinker™ support. Fully protected nucleoside phosphoramidites were incorporated using standard solid-phase oligonucleotide synthesis, i.e. 3% dichloroacetic acid in DCM for deblocking, 1 M 4,5-dicyanoimidazole 0.1 M N-methylimidazole in acetonitrile as activator for amidite couplings, acetic anhydride in THF and 10% 1-methylimidazole in THF/pyridine for capping, 0.02 M iodine in pyridine:water 9:1 (v:v) for oxidation and 0.1 M xanthene hydride in pyridine:acetonitrile 1:1 (v:v) for sulfurization. DNA and (S)-cEt building blocks were dissolved in acetonitrile (0.1 M) and incorporated using 2×4 min coupling time while morpholino diamidites (Compound 4 wherein R is thymine, prepared as per the procedure of Example 13) were dissolved in acetonitrile at 0.15 M and coupled for 2×6 min. At the end of the synthesis, the 5' DMT group was removed on support and cyanoethyl protecting groups removed using triethylamine:acetonitrile 1:1 (v:v). The remaining protecting groups were cleaved in concentrated aqueous ammonia at 55° C. for 8 hrs. The crude oligonucleotides were purified by ion-exchange-HPLC using a linear gradient of buffer A and B. Buffer A: 50 mM $NaHCO_3$ in acetonitrile:water 3:7 (v:v), buffer B: 1.5 M NaBr, 50 mM $NaHCO_3$ in acetonitrile:water 3:7 (v:v). The purified oligonucleotides were desalted using C18 reverse-phase cartridges.

Example 18

Thermal Stability Assay

A series of modified oligonucleotides were evaluated in a thermal stability ($T_m$) assay. A Cary 100 Bio spectrophotometer with the Cary Win UV Thermal program was used to measure absorbance vs. temperature. For the $T_m$ experiments, oligonucleotides were prepared at a concentration of 8 µM in a buffer of 100 mM Na+, 10 mM phosphate and 0.1 mM EDTA (pH 7). The concentration of the oligonucleotides was determined at 85° C. The concentration of each oligonucleotide was 4 µM after mixing of equal volumes of test oligonucleotide and complimentary RNA strand. Oligonucleotides were hybridized with the complimentary RNA strand by heating the duplex to 90° C. for 5 minutes followed by cooling to room temperature. Using the spectrophotometer, $T_m$ measurements were taken by heating the duplex solution at a rate of 0.5° C./min in cuvette starting @ 15° C. and heating to 85° C. $T_m$ values were determined using Vant Hoff calculations ($A_{260}$ vs temperature curve) using non self-complementary sequences where the minimum absorbance which relates to the duplex and the maximum absorbance which relates to the non-duplex single strand are manually integrated into the program. The oligonucleotides were hybridized to complementary phosphodiester linked DNA and or RNA as listed below.

In Table 1, 3/10/3 cEt gapmer oligonucleotides either unmodified or with 1 morpholino monomer located at position 4, 6, 7 or 9 were hybridized to complementary RNA for Tm measurement. All of the internucleoside linkages are phosphorothioate except that morpholino monomers are linked from the morpholino ring nitrogen by a phosphoramidate to the adjacent DNA monomer. The internucleoside linkages in the complementary RNA are phosphodiesters.

In Table 2, 12mer oligonucleotides that are either unmodified, have 3 morpholino monomers alternating with DNA monomers, or have a continuous sequence of 6 morpholino monomers which are hybridized to complementary RNA for Tm measurement. The alternating and continuous motifs were located internally in 12mers flanked on each side by 3 or 4 DNA monomers. Each of the internucleoside linkages are phosphodiester except that each morpholino monomer is linked from the morpholino ring nitrogen by a phosphoramidate to the adjacent DNA monomer at the 5' position. The internucleoside linkages in the complementary RNA are phosphodiesters.

The cEt and morpholino monomers are illustrated below. The results are presented in tables 1 and 2 below.

TABLE 1

| SEQ ID NO./ISIS #/*ION# | Composition (5' to 3') | Tm/ΔTm ° C. | Morpholino mods |
|---|---|---|---|
| 05/792775 | UAAUGUGAGAACAUGC | n/a | RNA compliment, PO |
| 06/558807 | $G_k{}^mC_kA_k$TGTT$^m$CT$^m$CA$^m$CAT$_kT_kA_k$ | 64.9/0.0 | unmodified, PS |
| 06/*1044689 | $G_k{}^mC_kA_kT_o$GTT$^m$CT$^m$CA$^m$CAT$_kT_kA_k$ | 56.7/-8.2 | morpholino at pos 4, PS |
| 06/*1044690 | $G_k{}^mC_kA_k$TG$T_oT^m$CT$^m$CA$^m$CAT$_kT_kA_k$ | 66.2/1.3 | morpholino at pos 6, PS |
| 06/*1044691 | $G_k{}^mC_kA_k$TGT$T_o{}^m$CT$^m$CA$^m$CAT$_kT_kA_k$ | 67.4/2.5 | morpholino at pos 7, PS |
| 06/*1044692 | $G_k{}^mC_kA_k$TGTT$^m$C$T_o{}^m$CA$^m$CAT$_kT_kA_k$ | 65.4/0.5 | morpholino at pos 9, PS |

TABLE 2

| SEQ ID NO./ISIS #/*ION# | Composition (5' to 3') | Tm/ΔTm ° C. (against DNA) | Tm/ΔTm ° C. period (against RNA) | Morpholino mods/ linkages PO |
|---|---|---|---|---|
| 08/438705 | GCGTTTTTTGCT | 50.6/0.0 | 45.6/0.0 | DNA |
| 08/*1051474 | GCG$T_o$TT$_o$TT$_o$TGCT | 59.1/2.8 | 56.5/3.6 | alternating |
| 08/*1051473 | GCG$T_oT_oT_oT_oT_oT_o$GCT | | 49.0/0.6 | continuous |
| 07/483795 | AGCAAAAAACGC | n/a | n/a | DNA compl. |
| 07/438704 | AGCAAAAAACGC | n/a | n/a | RNA compl. |

Nucleosides followed by a subscript "k" are (S)-cEt modified nucleosides, "T" indicates a morpholino monomer and all other monomers are β-D-2'-deoxyribonucleosides, "$^m$C" indicates a 5-methyl cytidine and subscript and italicized "o" indicates a 3'-phosphoramidate internucleoside linkage. The remainder of the internucleoside linkages in the oligonucleotide backbone are listed in the table as being "PS" phosphorothioate or "PO" phosphodiester.

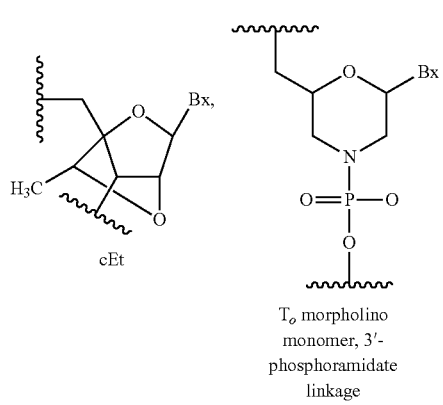

$T_o$ morpholino monomer, 3'-phosphoramidate linkage

Wherein Bx is a heterocyclic base.

Example 19

Modified Oligonucleotides Targeting CXCL12 In Vitro Study

Modified oligonucleotides were designed based on the control oligonucleotide ISIS 558807, as illustrated in Example 18. The 3/10/3 gapmer design was modified by incorporation of a single morpholino monomer at various positions within the gap region. Two morpholino modified oligonucleotides is prepared for each modified position to compare the effect of having a phosphate versus a thiophosphate linkage attaching the morpholino monomer to the 3'-adjacent β-D-2'-deoxy-ribonucleotide. The resulting modified oligonucleotides were tested for their ability to inhibit CXCL12 (Chemokine ligand 12) and Raptor mRNA expression levels. The potency of the modified oligonucleotides was evaluated and compared to the control oligonucleotide.

The oligonucleotides were tested in vitro in mouse b.END cells by electroporation. Cells at a density of 20,000 cells per well were transfected using electroporation with 0.027, 0.082, 0.25, 0.74, 2.22, 6.67 and 20 uM concentrations of each of the oligonucleotides listed below. After a treatment period of approximately 24 hours, RNA was isolated from the cells and mRNA levels were measured by quantitative real-time PCR and the CXCL12 mRNA and Raptor mRNA levels were adjusted according to total RNA content, as measured by RIBOGREEN®.

The half maximal inhibitory concentration ($IC_{50}$) of each oligonucleotide listed above was calculated by plotting the concentration of oligonucleotide versus the percent inhibition of CXCL12 mRNA or Raptor mRNA expression achieved at each concentration, and noting the concentration of oligonucleotide at which 50% inhibition of CXCL12 mRNA expression is achieved compared to the control. The results are presented in Table 3 below.

TABLE 3

| SEQ ID NO./ISIS #/*ION# | Composition (5' to 3') | CXCL12 IC50 (nM) | RAPTOR IC50 (nM) | morpholino linkage |
|---|---|---|---|---|
| 06/558807 | $G_k{}^mC_kA_k$TGTT${}^m$CT${}^m$CA${}^m$CAT$_kT_kA_k$ | 47 | 800 | Control |
| 06/*1044689 | $G_k{}^mC_kA_k\underline{T_o}$GTT${}^m$CT${}^m$CA${}^m$CAT$_kT_kA_k$ | 405 | >20000 | phosphoramidate |
| 06/*1048416 | $G_k{}^mC_kA_k\underline{T_s}$GTT${}^m$CT${}^m$CA${}^m$CAT$_kT_kA_k$ | 333 | >20000 | thiophosphoramidate |
| 06/*1044690 | $G_k{}^mC_kA_k$TG$\underline{T_o}$T${}^m$CT${}^m$CA${}^m$CAT$_kT_kA_k$ | 182 | 4100 | phosphoramidate |
| 06/*1048417 | $G_k{}^mC_kA_k$TG$\underline{T_s}$T${}^m$CT${}^m$CA${}^m$CAT$_kT_kA_k$ | 159 | 3300 | thiophosphoramidate |
| 06/*1044691 | $G_k{}^mC_kA_k$TGT$\underline{T_o}{}^m$CT${}^m$CA${}^m$CAT$_kT_kA_k$ | 128 | 4400 | phosphoramidate |
| 06/*1048418 | $G_k{}^mC_kA_k$TGT$\underline{T_s}{}^m$CT${}^m$CA${}^m$CAT$_kT_kA_k$ | 134 | 5200 | thiophosphoramidate |
| 06/*1044692 | $G_k{}^mC_kA_k$TGTT${}^m$C$\underline{T_o}{}^m$CA${}^m$CAT$_kT_kA_k$ | 145 | 1900 | phosphoramidate |
| 06/*1048419 | $G_k{}^mC_kA_k$TGTT${}^m$C$\underline{T_s}{}^m$CA${}^m$CAT$_kT_kA_k$ | 119 | 1100 | thiophosphoramidate |

Nucleosides followed by a subscript "k" are (S)-cEt modified nucleosides, "T" indicates a morpholino monomer and all other monomers are β-D-2'-deoxyribonucleosides, "${}^m$C" indicates a 5-methyl cytidine, subscript and italicized "o" indicates a 3'-phosphoramidate internucleoside linkage and subscript and italicized "s" indicates a 3'-thiophosphoramidate internucleoside linkage. All internucleoside linkages are phosphorothioate internucleoside linkages.

The invention claimed is:

1. A gapped oligomeric compound comprising from 10 to 30 monomer subunits, wherein the gapped oligomeric compound has a first region consisting of from 2 to 5 monomer subunits, a second region consisting of from 2 to 5 monomer subunits, and a gap region located between the first and second region consisting of from 8 to 12 monomer subunits, wherein each monomer subunit in the first and second regions is a modified nucleoside, and wherein the gap region comprises one monomer subunit having Formula III:

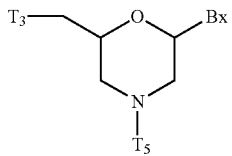

wherein independently for each monomer subunit having Formula III:
Bx is an optionally protected heterocyclic base moiety;
$T_3$ is an internucleoside linking group linking the monomer subunit of Formula III to the 5'-remainder of the oligomeric compound;
$T_5$ is a linking group having the formula:

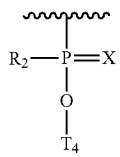

wherein independently for each $T_5$:
$R_2$ is hydroxyl, $C_{1-6}$ alkyl, or substituted $C_{1-6}$ alkyl comprising an optionally protected substituent group selected from halogen, $OJ_1$, $NJ_1J_2$, $SJ_1$, $N_3$, $OC(=Q)J_1$, $OC(=Q)NJ_1J_2$, $NJ_3C(=Q)NJ_1J_2$, and CN, wherein each $J_1$, $J_2$, and $J_3$ is, independently, H or $C_1$-$C_6$ alkyl, and Q is O, S, or $NJ_1$;

X is O or S, wherein when X is O, at least one $R_2$ is other than hydroxyl; and
$T_4$ is a single bond connecting said linking group to the 3'-remainder of the oligomeric compound;
wherein each monomer subunit in the gap region other than monomer subunits having Formula III is a β-D-2'-deoxyribonucleoside; and wherein the monomer having Formula III is located at position 1, 2, 3, or 4 from the 5' end of the gap.

2. The oligomeric compound of claim 1, wherein each Bx is, independently, uracil, thymine, cytosine, 4-N-benzoylcytosine, 4-N-isobutyrylcytosine, 5'-methyl cytosine, 5'-methyl-4-N-benzoylcytosine, 5'-methyl-4-N-isbutyrylcytosine, adenine, 6-N-benzoyladenine, guanine, or 2-N-isobutyrylguanine.

3. The oligomeric compound of claim 1, wherein each X is O.

4. The oligomeric compound of claim 1, wherein each $R_2$ is hydroxyl, methyl, or —$(CH_2)_3$—$OCH_3$.

5. The oligomeric compound of claim 1, wherein each modified nucleoside in the first and second region comprises a modified sugar moiety.

6. The oligomeric compound of claim 1, wherein at least one modified nucleoside in the first and second region comprises a sugar surrogate.

7. A method of inhibiting gene expression comprising contacting one or more cells, a tissue, or an animal with an oligomeric compound of claim 1, wherein said oligomeric compound is complementary to a target RNA.

8. The oligomeric compound of claim 1, wherein the monomer having Formula III is located at position 1 from the 5' end of the gap.

9. The oligomeric compound of claim 1, wherein the monomer having Formula III is located at position 3 from the 5' end of the gap.

* * * * *